(12) United States Patent
During

(10) Patent No.: US 11,364,228 B2
(45) Date of Patent: Jun. 21, 2022

(54) GABOXADOL FOR THERAPEUTIC TREATMENT OF 1P36 DELETION SYNDROME

(71) Applicant: Ovid Therapeutics Inc., New York, NY (US)

(72) Inventor: Matthew During, Weston, CT (US)

(73) Assignee: Ovid Therapeutics Inc., New York, NY (US)

(*) Notice: Subject to any disclaimer, the term of this patent is extended or adjusted under 35 U.S.C. 154(b) by 0 days.

(21) Appl. No.: 17/126,168

(22) Filed: Dec. 18, 2020

(65) Prior Publication Data

US 2021/0186938 A1 Jun. 24, 2021

Related U.S. Application Data

(60) Provisional application No. 62/949,551, filed on Dec. 18, 2019.

(51) Int. Cl.
*A61K 31/4355* (2006.01)
*A61K 31/437* (2006.01)

(52) U.S. Cl.
CPC .................................. *A61K 31/437* (2013.01)

(58) Field of Classification Search
CPC .... A61K 31/4355; A61K 31/437; A61P 25/00
USPC ........................................................ 514/302
See application file for complete search history.

(56) References Cited

U.S. PATENT DOCUMENTS

| | | |
|---|---|---|
| 5,929,065 A | 7/1999 | Lancel |
| 8,022,084 B2 | 9/2011 | Kumke et al. |
| 8,236,958 B2 | 8/2012 | Cooper |
| 9,339,495 B2 | 5/2016 | During |
| 9,399,034 B1 | 7/2016 | During et al. |
| 9,446,028 B2 | 9/2016 | During |
| 9,682,069 B2 | 6/2017 | During |
| 9,717,716 B2 | 8/2017 | During et al. |
| 9,744,159 B2 | 8/2017 | During |
| 9,801,864 B2 | 10/2017 | During |
| 10,188,635 B2 | 1/2019 | During |
| 10,363,246 B1 | 7/2019 | During |
| 10,603,308 B2 | 3/2020 | During |
| 11,096,929 B2 * | 8/2021 | During ................. A61K 31/437 |
| 2002/0165217 A1 | 11/2002 | Howard |
| 2005/0137222 A1 | 6/2005 | Ebert et al. |
| 2005/0234093 A1 | 10/2005 | Sanchez et al. |
| 2007/0032553 A1 | 2/2007 | McKernan et al. |
| 2007/0112017 A1 | 5/2007 | Barlow et al. |
| 2007/0259912 A1 | 11/2007 | Cooper |
| 2008/0269278 A1 | 10/2008 | Lundahl et al. |
| 2009/0048288 A1 | 2/2009 | Ebert et al. |
| 2009/0143335 A1 | 6/2009 | Larsen et al. |
| 2009/0203731 A1 | 8/2009 | Sanchez et al. |
| 2009/0269795 A1 | 10/2009 | Smith |
| 2010/0093787 A1 | 4/2010 | Lundahl et al. |
| 2011/0046090 A1 | 2/2011 | Barlow et al. |
| 2012/0035207 A1 | 2/2012 | McKernan et al. |
| 2015/0313913 A1 | 11/2015 | Catterall et al. |
| 2015/0352085 A1 | 12/2015 | During |
| 2017/0014392 A1 | 1/2017 | During |
| 2017/0014393 A1 | 1/2017 | During |
| 2017/0037475 A1 | 2/2017 | Ho et al. |
| 2017/0348232 A1 | 12/2017 | During |
| 2018/0042903 A1 | 2/2018 | During |
| 2018/0098974 A1 | 4/2018 | During |
| 2018/0344708 A1 | 12/2018 | During |
| 2019/0038606 A1 | 2/2019 | During |

FOREIGN PATENT DOCUMENTS

| | | |
|---|---|---|
| DE | 102005020882 A1 | 11/2006 |
| EP | 0840601 B1 | 10/2001 |
| EP | 1337247 B1 | 8/2006 |
| EP | 1641456 B1 | 3/2010 |
| GB | 2410434 A | 8/2005 |
| JP | 2012501301 A | 1/2012 |
| WO | 9702813 A1 | 1/1997 |
| WO | 2005023256 A1 | 3/2005 |
| WO | 2005058313 A1 | 6/2005 |
| WO | 2005094820 A1 | 10/2005 |
| WO | 2006013397 A1 | 2/2006 |
| WO | 2006118897 A1 | 11/2006 |
| WO | 2009021521 A2 | 2/2009 |
| WO | 2009056146 A1 | 5/2009 |
| WO | 2010015037 A1 | 2/2010 |
| WO | 2014123909 A1 | 8/2014 |
| WO | 2017015049 A1 | 1/2017 |

OTHER PUBLICATIONS

Walter Alexander, "Sleep: Gaboxadol Enhances Slow Wave Sleep," Perelman, School of Medicine, Jun. 22, 2006; 3 pages.
Bahi-Buisson et al., "CDKL5-Related Disorders: From Clinical Description to Molecular Genetics," Molecular Syndromology, 2011, vol. 2; pp. 137-152.

(Continued)

*Primary Examiner* — Charanjit Aulakh
(74) *Attorney, Agent, or Firm* — Carter, DeLuca & Farrell LLP

(57) ABSTRACT

Methods and pharmaceutical compositions containing gaboxadol or a pharmaceutically acceptable salt thereof for treating 1p36 deletion syndrome are provided.

21 Claims, No Drawings

(56) References Cited

OTHER PUBLICATIONS

Cheng et al., "Inducing Anesthesia with a GABA Analog, THIP,", Anesthesiology, vol. 63, No. 2, Aug. 1985; pp. 147-151.
Ebert et al., "Treating Insomnia: Current and Investigational Pharmacological Approaches," Pharmacology & Therapeutics, vol. 112, 2006; pp. 612-629.
Deacon et al., "Effect of Short-Term Treatment with Gaboxadol on Sleep Maintenance and Initiation in Patients with Primary Insomnia," Sleep, vol. 30, No. 3, 2007; pp. 281-287.
National Institutes of Health, U.S. National Library of Medicine, ip36 deletion syndrome, Jan. 2014; 5 pages.
Walsh et al. "The Selective Extrasynaptic GABAA Agonist, Gaboxadol, Improves Traditional Hypnotic Efficacy Measures and Enhances Slow Wave Activity in a Model of Transient Insomnia," Sleep, vol. 30, No. 5, 2007; pp. 593-602.
Stephanie Saul, "Merck Cancels Work on a New Insomnia Medication," The New York Times, Mar. 29, 2007; 2 pages.
James K. Walsh, Ph D., "Enhancement of Slow Wave Sleep: Implications for Insomnia," Journal of Clinical Sleep Medicine, Supplement to vol. 5, No. 2, (2009); pp. 827-832.
Faulhaber et al., "The GABAA Agonist THIP Produces Slow Wave Sleep and Reduces Spindling Activity in NREM Sleep in Humans," Psychopharmacology, vol. 130, 1997; pp. 285-291.
Gaboxadol, from Wikipedia, the free encylopedia,http://en.wikipedia.org/wiki/Gaboxadol, 2014; 2 pages.
Gaboxadol, Investigational Agent—Drug Development Technology, http//www.drugdevelopment-technology.com/projects/gaboxadol-2014; 3 pages.
Gaboxadol, Bluelight, http://www.bluelight.org/vb/threads/370965-Gaboxadol-(2014); 1 page.
Glykys et al., "The Main Source of Ambient GABA Responsible for Tonic Inhibition in the Mouse Hippocampus," J Physiol, (2007), vol. 582, No. 3; pp. 1163-1178.
Hajak et al., "A 2-week Efficacy and Safety Study of Gaboxadol and Zolpidem Using Electronic Diaries in Primary Insomnia Outpatients," Sleep Medicine, vol. 10, 2009; pp. 705-712.
Jennum et al., "Sleep Disorders in Neurodegenerative Disorders and Stroke," European Handbook of Neurological Management, vol. 1, 2nd Edition, Chapter 39, Section 6—Sleep Disorders, (Ed. Gilhus et al.) Blackwell Publishing Ltd. 2011; pp. 529-543.
Jonas et al., "Neural Inhibition,", Scholarpedia—http://www.scholarpedia.org/article/Neural.sub.-inhibition-—(2014); 10 pages.
Lancel et al., "The GABAA Agonist THIP (Gaboxadol) Increases Non-REM Sleep and Enhances Delta Activity in the Rat," Sleep and Rhythms, NeuroReport, Rapid Science Publishers, vol. 7, No. 13; Sep. 1996; pp. 2241-2245.
Marike Lancel, "The GABAA Agonist THIP Increases Non-REM Sleep and Enhances Non-REM Sleep-Specific Delta Activity in the Rat During the Dark Period," Sleep, vol. 20, No. 12, American Sleep Disorders Association and Sleep Research Society (1997); pp. 1099-1104.
Marike Lancel, "Role of GABAA Receptors in the Regulation of Sleep: Initial Sleep Responses to Peripherally Administered Modulators and Agonists," Sleep, vol. 22, No. 1, (1999); pp. 33-42.
Lancel et al., "Effect of the GABAA Agonist Gaboxadol on Nocturnal Sleep and Hormone Secretion in Healthy Elderly Subjects," Am J. Physiol Endoctrinol Metab, vol. 281; (2001), pp. E130-E137.
Larsen et al.,—Research Paper—"Intestinal Gaboxadol Absorption via PAT1 (SLC36A1): Modified Absorption in vivo Following Co-administration of L-tryptophan," British Journal of Pharmacology (BJP), vol. 157, (2009); pp. 1380-1389.
Mathias et al., "The GABAA Agonist Gaboxadol Improves the Quality of Post-Nap Sleep," Psychopharmacology, vol. 157 (2001); pp. 299-304.
Mathias et al., "Effect of Repeated Gaboxadol Administration on Night Sleep and Next-Day Performance in Healthy Elderly Subjects," Neuropsychopharmacology, vol. 30, (2005) pp. 833-841.
International Search Report and Written Opinion of the International Searching Authority, dated Sep. 27, 2016, corresponding to International Application No. PCT/US16/42238; 8 total pages.
Egawa et al., "Pathophysiological power of improper tonic GABA(A) conductances in mature and immature models." Frontiers in Neural Circuits, Oct. 24, 2013, vol. 7, Article 170; pp. 1-15.
PCT Notice concerning Transmittal of International Preliminary Report on Patentability (Chapter I of the Patent Cooperation Treaty), International Preliminary Report on Patentability and Written Opinion of the International Searching Authority,dated Feb. 1, 2018, corresponding to International Application No. PCT/US2016/042238; 8 total pages.
Reagan-Shaw et al., "Dose translation from animal to human studies revisited", FASEB J, vol. 22, No. 3, Oct. 17, 2007; pp. 659-661.
International Search Report and Written Opinion of the International Searching Authority, dated Aug. 14, 2015, corresponding to International Application No. PCT/US2015/029155; 19 total pages.
Oakley et al., "Synergistic GABA—Enhancing Therapy against Seizures in a Mouse Model of Dravet Syndrome," The Journal of Pharmacology and Experimental Therapeutics, vol. 345, May 2013; pp. 215-224.
Kesisoglou et al., "Utility of PBPK Absorption Modeling to Guide Modified Release Formulation Development of Gaboxadol, a Highly Soluble Compound with Region-Dependent Absorption," Research Article—Pharmaceutics, Drug Delivery and PharmaceuticalTechnology, Aug. 19, 2015; Journal of Pharmacetuical Sciences, vol. 105 (2016); pp. 722-728 (7 pages).
Boyle et al., "Next-day residual effects of gaboxadol and flurazepam administered at bedtime: a randomized doubleMind study in healthy elderly subjects," Human Psychopharmacology, 2009, vol. 24, pp. 61-71.
Peixoto et al., "Effects of gabaergic drugs on reserpine-induced oral dyskinesia," Behavioural Brain Research, vol. 160, (2005); pp. 51-59.
Chilean Office Action dated Feb. 13, 2019, corresponding to Chilean Application No. 201800142; 7 pages.
Lundahl et al., "Short-term Treatment with Gaboxadol Improves Sleep Maintenance and Enhances Slow Wave Sleep n Adult Patients with Primary Insomnia," Psychopharmacology, vol. 195, (2007); pp. 139-146.
International Search Report and Written Opinion of the International Searching Authority, dated Apr. 24, 2018, corresponding to International Application No. PCT/US18/16602; 15 total pages.
International Search Report and Written Opinion, dated Oct. 4, 2016, corresponding to International Application No. PCT/US16/50702; 9 total pages.
International Search Report and Written Opinion of the International Searching Authority, dated Jul. 18, 2017, corresponding to International Application No. PCT/US17/34443; 5 total pages.
International Search Report and Written Opinion of the International Searching Authority, dated Aug. 26, 2015, corresponding to International Application No. PCT/US15/34018; 12 total pages.
International Search Report and Written Opinion, dated Oct. 31, 2017, corresponding to International Applicaiton No. PCT/US17/46256; 10 total pages.
Loescher, W., "Development of Tolerance to the Anticonvulsant Effect of GABA-mimetic Drugs in Animal Models of Seizure States in Tolerance to Beneficial and Adverse Effects of Antiepileptic Drugs," Koella et al. (eds.), pp. 37-45 4986).
Petersen et al., "THIP: A Single Blind Controlled Trial in Patients with Epilepsy," Acta Neurol. Scand. 67; pp. 114-117 (1983).
Notification Concerning Transmittal of International Preliminary Report on Patentability, dated Jun. 6, 2019, International Preliminary Report on Patentability dated May 28, 2019, corresponding to counterpart International Application No. PCT/US2017/062685 and Written Opinion of the International Searching Authority corresponding to counterpart Application No. PCT/US2017/062685; 11 total pages.
International Search Report and Written Opinion of the International Searching Authority, dated Jan. 31, 2020, corresponding to counterpart International Application No. PCT/US2019/052085; 13 total pages.

(56) References Cited

OTHER PUBLICATIONS

International Search Report and the Written Opinion of the International Searching Authority, dated Jul. 1, 2019, corresponding to counterpart International Application No. PCT/US19/26218; 10 total pages.
European Search Report dated Feb. 13, 2019, corresponding to European Application No. 16828266.3; 11 pages.
Jordan et al., The Application of Clinical Genetics 2015:8 189-200.
International Serach Report and Written Opinion dated Mar. 8, 2021, corresponding to counterpart International Application No. PCT/US2020/065801; 9 total pages.

* cited by examiner

GABOXADOL FOR THERAPEUTIC TREATMENT OF 1P36 DELETION SYNDROME

CROSS-REFERENCE TO RELATED APPLICATION

This application claims benefit of and priority to U.S. Provisional Application No. 62/949,551, filed Dec. 18, 2019, which is incorporated by reference in its entirety.

TECHNICAL FIELD

Treatment of 1p36 Deletion syndrome with gaboxadol or a pharmaceutically acceptable salt thereof are provided.

BACKGROUND

Gaboxadol (4,5,6,7-tetrahydroisoxazolo [5,4-c]pyridine-3-ol) (THIP)) is described in EP Patent No. 0000338 and in EP Patent No. 0840601, U.S. Pat. Nos. 4,278,676, 4,362,731, 4,353,910, and WO 2005/094820. Gaboxadol is a selective $GABA_A$ receptor agonist with a preference for 6-subunit containing $GABA_A$ receptors. Gaboxadol is an agonist of GABA receptors that contain $\alpha_4$, $\alpha_6$, and $\delta$ subunits, which have more restricted anatomic distribution in the thalamus, hippocampus, and cerebellum and are mainly extrasynaptic in location. Gaboxadol has its greatest efficacy at $\alpha 4\beta\delta$ and $\alpha 6\beta\delta$ $GABA_A$ receptors, that is, benzodiazepine-insensitive receptors that contribute to tonic inhibitory conductances rather than synaptic inhibitory postsynaptic currents. Accordingly, the mode of action and effects of gaboxadol are distinct from those of benzodiazepine receptor agonists. Extrasynaptic GABA receptors are sensitive to low concentrations of GABA, they desensitize slowly, and their activation can induce sustained neuronal effects. In conventional pharmaceutical compositions such as tablets and capsules, gaboxadol is rapidly absorbed, reaching peak concentration within 30 minutes, with a half-life of approximately 1.5 to 2 hours. Gaboxadol is a zwitterion with pKa values of 4.3 (acidic) and 8.3 (basic) and log P of _0.61. Gaboxadol is highly soluble, more than 30 mg/mL in the physiological pH range.

In the early 1980s gaboxadol was the subject of a series of pilot studies that tested its efficacy as an analgesic and anxiolytic, as well as a treatment for tardive dyskinesia, Huntington's disease, Alzheimer's disease, and spasticity. In the 1990s gaboxadol moved into late stage development for the treatment of insomnia. The development was discontinued after the compound failed to show significant effects in sleep onset and sleep maintenance in a three-month efficacy study. Additionally, patients with a history of drug abuse who received gaboxadol experienced a steep increase in psychiatric adverse events.

1p36 deletion syndrome, also known as 1p36 monosomy, is a chromosomal disorder caused by a deletion of genetic material from a specific region in the short (p) arm of chromosome 1. See, National Institutes of Health, US National Library of Medicine, Genetics Home Reference, https://ghr.nlm.nih.gov/condition/1p36-deletion-syndrome. Deletions of chromosome 1p36 affect approximately 1 in 5,000 newborns and constitute the most common terminal chromosomal deletion in humans. See, Jordan et al., The Application of Clinical Genetics 2015:8 189-200. A pattern of characteristic functional deficits, congenital anomalies, and physical features associated with 1p36 deletions has emerged. Id. This pattern includes developmental delay, intellectual disability, seizures, vision problems, hearing loss, short stature, brain anomalies, orofacial clefting, congenital heart defects, cardiomyopathy, renal anomalies, and distinctive facial features—straight eyebrows, deeply set eyes, midface retrusion, wide and depressed nasal bridge, long philtrum, pointed chin, large, late-closing anterior fontanel, microbrachycephaly, epicanthal folds, and posteriorly rotated, low-set, abnormal ears. Id. Defining this pattern made the 1p36 deletion syndrome a clinically recognizable entity. Id.

According to the National Institutes of Health, supra, 1p36 deletion syndrome typically causes severe intellectual disability. Most affected individuals do not speak, or speak only a few words. They may have temper tantrums, self-harming behavior such as biting themselves, or may exhibit other behavior problems. Most have structural abnormalities of the brain, and seizures occur in more than half of individuals with this disorder. Affected individuals usually have weak muscle tone (hypotonia) and swallowing difficulties (dysphagia). Other features include a small head that is unusually short and wide; vision and hearing problems; abnormalities of the skeleton, heart, gastrointestinal system, kidneys, or genitalia; and distinctive facial features. Most cases are not inherited; only about 20% of the cases of people with 1p36 deletion syndrome inherit the chromosome with a deleted segment from an unaffected parent. The following genes have been implicated in the development of various 1p36 deletion syndrome phenotypes: MMP23B, GABRD, SKI, PRDM16, KCNAB2, RERE, UBE4B, CASZ1, PDPN, SPEN, ECE1, HSPG2, and LUZP1. See, Jordan et al., supra.

There is no cure for 1p36 deletion syndrome. Treatment is focused on relieving symptoms of the disease. There remains a need for effective treatment of 1p36 deletion syndrome.

SUMMARY

Treatment of 1p36 deletion syndrome with gaboxadol or a pharmaceutically acceptable salt thereof is provided. In embodiments, about 5 mg to about 50 mg gaboxadol or a pharmaceutically acceptable salt thereof is administered to a patient having 1p36 deletion syndrome. In embodiments, about 5 mg to about 50 mg gaboxadol or a pharmaceutically acceptable salt thereof is administered twice daily to a patient having 1p36 deletion syndrome. In embodiments, about 5 mg to about 50 mg gaboxadol or a pharmaceutically acceptable salt thereof is administered three times daily to a patient having 1p36 deletion syndrome. In embodiments, pharmaceutical compositions include about 5 mg to about 50 mg gaboxadol or a pharmaceutically acceptable salt thereof and are administered to a patient having 1p36 deletion syndrome.

In embodiments, a method for treating 1p36 deletion syndrome includes administering to a patient in need thereof from about 20 mg to about 50 mg gaboxadol or a pharmaceutically acceptable salt thereof. In embodiments, a method for treating 1p36 deletion syndrome includes administering to a patient in need thereof from about 20 mg to about 50 mg gaboxadol or a pharmaceutically acceptable salt thereof, once twice or three times a day. In embodiments, a method for treating 1p36 deletion syndrome includes administering to a patient in need thereof a pharmaceutical composition including from about 50 mg to about 250 mg gaboxadol or a pharmaceutically acceptable salt thereof.

In embodiments, gaboxadol or a pharmaceutically acceptable salt thereof is used to manufacture a pharmaceutical composition for treating 1p36 deletion syndrome. Pharmaceutical compositions herein include conventional dosage forms and modified release dosage forms. In embodiments, the pharmaceutical composition is an orally disintegrating dosage form. In embodiments, the pharmaceutical composition is an extended release dosage form. In embodiments, the extended release dosage form releases the gaboxadol or a pharmaceutically acceptable salt thereof for 6 or more hours after administration. In embodiments, the extended release dosage form releases the gaboxadol or a pharmaceutically acceptable salt thereof for 12 or more hours after administration. In embodiments, the pharmaceutical composition is a delayed release dosage form. In embodiments, the pharmaceutical composition is a pulsatile release dosage form.

In embodiments, treatment of 1p36 deletion syndrome includes administering to a patient age 1 month to 18 years and in need thereof from about 1 mg to about 50 mg gaboxadol or a pharmaceutically acceptable salt thereof. In embodiments, treatment of 1p36 deletion syndrome with gaboxadol or a pharmaceutically acceptable salt thereof reduces or alleviates one or more symptoms of 1p36 deletion syndrome.

DETAILED DESCRIPTION

Described herein are methods for treating 1p36 deletion syndrome by administering to a patient in need thereof gaboxadol or a pharmaceutically acceptable salt thereof. Also described herein are pharmaceutical compositions including gaboxadol or a pharmaceutically acceptable salt thereof that are used for treating 1p36 deletion syndrome. In embodiments, pharmaceutical compositions and methods are described herein for treating 1p36 deletion syndrome that involve administering to a patient in need thereof a conventional pharmaceutical composition including gaboxadol or a pharmaceutically acceptable salt thereof. In embodiments, pharmaceutical compositions and methods are described herein for treating 1p36 deletion syndrome that involve administering to a patient in need thereof a modified release pharmaceutical composition including gaboxadol or a pharmaceutically acceptable salt thereof. In embodiments, pharmaceutical compositions and methods are described herein for treating 1p36 deletion syndrome involve administering to a patient in need thereof a transdermal pharmaceutical composition including gaboxadol or a pharmaceutically acceptable salt thereof.

As mentioned above, certain genes have been implicated in the development of various 1p36 deletion syndrome phenotypes. Haploinsufficiency of the gamma-aminobutyric acid (GABA) A receptor, delta gene (GABRD; chr1:1,950,768-1,962,192; OMIM# 137163) has been suggested as a possible contributor to the neurodevelopmental abnormalities, neuropsychiatric problems, and seizures seen in children with 1p36 deletions. See, Jordan et al., supra. Accordingly, most young children with 1p36 deletion syndrome have delayed development of speech and motor skills. Speech can be severely affected, with many children learning only a few words or having no speech at all. Behavioral problems are also common, and include temper outbursts, banging or throwing objects, striking people, screaming episodes, and self-injurious behavior (wrist biting, head striking/banging). A significant proportion of affected people are on the autism spectrum, and many exhibit stereotypy, which is a repetitive or ritualistic movement, posture, or utterance. Stereotypies may be simple movements such as body rocking, or complex, such as self-caressing, crossing and uncrossing of legs, and marching in place. Treatment of a patient having 1p36 deletion syndrome with relatively high doses of gaboxadol or a pharmaceutically acceptable salt thereof as described herein can reduce or alleviate one or more of the foregoing symptoms of 1p36 deletion syndrome.

Methods of treating 1p36 deletion syndrome by administering to a patient in need thereof an effective amount of gaboxadol or a pharmaceutically acceptable salt thereof are provided. An effective amount or therapeutically effective amount can be a dose sufficient to treat, inhibit, or alleviate one or more symptoms of 1p36 deletion syndrome such as reducing the frequency or severity of seizures, reducing behaviorial problems (or otherwise improving behavior), reducing stereotypy; or to provide a desired pharmacologic and/or physiologic effect, for example, reducing, inhibiting, or reversing one or more of the underlying pathophysiological mechanisms underlying the 1p36 deletion syndrome. The precise dosage will vary according to a variety of factors such as subject-dependent variables (e.g., age, immune system health, clinical symptoms etc.).

Many pharmaceutical products are administered as a fixed dose, at regular intervals, to achieve therapeutic efficacy. The duration of action is typically reflected by plasma half-life of the drug post administration. Gaboxadol has a relatively short half-life ($t_{1/2}$=1.5-2 h). Since efficacy is often dependent on rapid onset of action and sufficient exposure within the central nervous system, administration of CNS drugs with a short half-life may require frequent maintenance dosing.

Different clinical situations frequently require different therapeutic approaches. For example, treatment of an acute symptomatic episode may call for a dosage form which facilitates a rapid onset of action for fast relief of acute symptoms resulting from 1p36 deletion syndrome. For example, an immediate need for reducing or alleviating seizures, self-harming behavior or a severe temper tantrum. Parenteral administration such as intravenous administration of a drug typically results in a more rapid onset of action than, for example, a conventional tablet or capsule composition, which must be swallowed and disintegrated in the stomach before the drug can be absorbed. However, parenteral administration can be inconvenient in a non-clinical setting.

Conventional (or unmodified) dosage forms do not involve formulations or incorporate ingredients that substantially change or interfere with absorption rates, onset of action. $C_{max}$ or $T_{max}$ of gaboxadol or a pharmaceutically acceptable salt thereof in the patient. In embodiments, a conventional oral dosage form is a solid dosage form, for example, a tablet, a caplet, a hard gelatin capsule, a starch capsule, a hydroxypropyl methylcellulose (HPMC) capsule, or a soft elastic gelatin capsule. In embodiments, a conventional oral dosage form can be a liquid such as a syrup, a suspension or a solution. Conventional oral dosage forms such as tablets, caplets or capsules typically release medications into the stomach or intestines as the tablet, caplet, or capsule shell dissolves. Suppositories for rectal or vaginal administration are also conventional dosage forms. Conventional dosage forms may be prepared using a pharmaceutically acceptable "carrier" composed of materials that are considered safe and effective. The "carrier" includes all components present in the pharmaceutical formulation other than the active ingredient or ingredients. The term "carrier" includes, but is not limited to, diluents, binders, lubricants, disintegrants, fillers, and coating compositions. In embodiments, a conventional dosage form can be a parenteral formulation, e.g., a solution, suspension, or emulsion for injection or infusion, or a powder for injection or infusion. Those skilled in the art are familiar with manufacture of conventional dosage forms. See, e.g., Remington: The Science and Practice of Pharmacy, 22$^{nd}$ revised edition, Pharmaceutical Press, 2012.

In embodiments, pharmaceutical compositions for treating 1p36 deletion syndrome are provided which are conventional dosage forms that include about 1 mg to about 50 mg of gaboxadol or a pharmaceutically acceptable salt thereof. For example, a conventional dosage form can include 1 mg, 2 mg, 3 mg, 4 mg, 5 mg 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, or 50 mg gaboxadol or a pharmaceutically acceptable salt thereof. In embodiments, the composition provides improvement in symptoms of 1p36 deletion syndrome in the patient for more than 6 hours after administration of the composition to the patient.

In embodiments, relatively high doses to treat 1p36 deletion syndrome administered as a child (one year to 18 years) or adult single dose may include amounts of gaboxadol or a pharmaceutically acceptable salt thereof in the range of about, e.g., 5 mg to 10 mg, 15 mg to 20 mg, 15 mg to 25 mg, 15 mg to 30 mg, 15 mg to 35 mg, 15 mg to 40 mg, 15 mg to 45 mg, 15 mg to 50 mg, 15 mg to 55 mg, 15 mg to 60 mg, 15 mg to 65 mg, 15 mg to 70 mg, 15 mg to 75 mg, 20 mg to 25 mg, 20 mg to 30 mg, 20 mg to 35 mg, 20 mg to 40 mg, 20 mg to 45 mg, 20 mg to 50 mg, 20 mg to 55 mg, 20 mg to 60 mg, 20 mg to 65 mg, 20 mg to 70 mg, 20 mg to 75 mg, 25 mg to 30 mg, 25 mg to 35 mg, 25 mg to 40 mg, 25 mg to 45 mg, 25 mg to 50 mg, 25 mg to 55 mg, 25 mg to 60 mg, 25 mg to 65 mg, 25 mg to 70 mg, 25 mg to 75 mg, 30 mg to 35 mg, 30 mg to 40 mg, 30 mg to 45 mg, 30 mg to 50 mg, 30 mg to 55 mg, 30 mg to 60 mg, 30 mg to 65 mg, 30 mg to 70 mg, 30 mg to 75 mg, 35 mg to 40 mg, 35 mg to 45 mg, 35 mg to 50 mg, 35 mg to 55 mg, 35 mg to 60 mg, 35 mg to 65 mg, 35 mg to 70 mg, 35 mg to 75 mg, 40 mg to 45 mg, 40 mg to 50 mg, 40 mg to 55 mg, 40 mg to 60 mg, 40 mg to 65 mg, 40 mg to 70 mg, 40 mg to 75 mg, 45 mg to 50 mg, 45 mg to 55 mg, 45 mg to 60 mg, 45 mg to 65 mg, 45 mg to 70 mg, 45 mg to 75 mg, 50 mg to 55 mg, 50 mg to 60 mg, 50 mg to 65 mg, 50 mg to 50 mg, or 50 mg to 75 mg.

Examples of relatively high child (depending on age and/or weight) or adult single doses of gaboxadol or a pharmaceutically acceptable salt thereof to treat 1p36 deletion syndrome are 10 mg, 15 mg, 20 mg, 25 mg, 30 mg, 35 mg, 40 mg, 45 mg, 50 mg, 55 mg, 60 mg, 65 mg, 70 mg, or 75 mg.

Typically, doses of gaboxadol or a pharmaceutically acceptable salt thereof are administered once daily, twice daily or three times daily to a patient in need thereof. The methods and compositions described herein may provide reduced dosing frequency and reduced adverse events and/or increased efficacy. In embodiments, the dosage is about, e.g., 10 mg to 150 mg/day, 15 mg to 150 mg/day, 20 mg to 150 mg/day, 25 mg to 150 mg/day, 30 mg to 150 mg/day, 35 mg to 150 mg/day, 40 mg to 150 mg/day, 45 mg to 150 mg/day, 50 mg to 150 mg/day, 55 mg to 150 mg/day, 60 mg to 150 mg/day, 65 mg to 150 mg/day, 70 mg to 150 mg/day, 75 mg to 150 mg/day, 80 mg to 150 mg/day, 85 mg to 150 mg/day, 90 mg to 150 mg/day, 95 mg to 150 mg/day, 100 mg to 150 mg/day, 105 mg to 150 mg/day, 110 mg to 150 mg/day, 115 mg to 150 mg/day, 120 mg to 150 mg/day, 125 mg to 150 mg/day, 130 mg to 150 mg/day, 135 mg to 150 mg/day, 140 mg to 150 mg/day, 145 mg to 150 mg/day, 15 mg to 225 mg/day, 20 mg to 225 mg/day, 25 mg to 225 mg/day, 30 mg to 225 mg/day, 35 mg to 225 mg/day, 40 mg to 225 mg/day, 45 mg to 225 mg/day, 50 mg to 225 mg/day, 55 mg to 225 mg/day, 60 mg to 225 mg/day, 65 mg to 225 mg/day, 70 mg to 225 mg/day, 75 mg to 225 mg/day, 80 mg to 225 mg/day, 85 mg to 225 mg/day, 90 mg to 225 mg/day, 95 mg to 225 mg/day, 100 mg to 225 mg/day, 105 mg to 225 mg/day, 110 mg to 225 mg/day, 115 mg to 225 mg/day, 120 mg to 225 mg/day, 125 mg to 225 mg/day, 130 mg to 225 mg/day, 135 mg to 225 mg/day, 140 mg to 225 mg/day, 145 mg to 225 mg/day, 150 mg to 225 mg/day, 155 mg to 225 mg/day, 160 mg to 225 mg/day, 165 mg to 225 mg/day, 170 mg to 225 mg/day, 175 mg to 225 mg/day, 180 mg to 225 mg/day, 185 mg to 225 mg/day, 190 mg to 225 mg/day, 200 mg to 225 mg/day, 205 mg to 225 mg/day, 210 mg to 225 mg/day, 215 mg to 225 mg/day, or 220 mg to 225 mg/day. For example, gaboxadol or a pharmaceutically acceptable salt thereof can be administered 10 mg/day, 15 mg/day, 20 mg/day, 25 mg/day, 30 mg/day, 35 mg/day, 40 mg/day, 45 mg/day, 50 mg/day, 55 mg/day, 60 mg/day, 65 mg/day, 70 mg/day, 75 mg/day, 80 mg/day, 85 mg/day, 90 mg/day, 100 mg/day, 105 mg/day, 115 mg/day, 120 mg/day, 125 mg/day, 130 mg/day, 135 mg/day, 140 mg/day, 145 mg/day, 150 mg/day, 155 mg/day, 160 mg/day, 165 mg/day, 170 mg/day, 175 mg/day, 180 mg/day, 190 mg/day, 195 mg/day, 200 mg/day, 205 mg/day, 210 mg/day, 215 mg/day, 220 mg/day, or 225 mg/day. In embodiments, gaboxadol or a pharmaceutically acceptable salt thereof is administered at doses of 1 mg, 2 mg, 3 mg, 4 mg, 5 mg, 6 mg, 7 mg, 8 mg, 9 mg, 10 mg, 11 mg, 12 mg, 13 mg, 14 mg, 15 mg to infants (1 month to 1 year) with 1p36 deletion syndrome, once, twice or three times daily. Pediatric (age 6 months to 12 years) doses can range from 2 mg/day to any of the amounts provided above, wherein higher amounts can be given to older children. Adolescent (age 12 years to 18 years) doses can range from 10 mg/day to any of the amounts provided above, wherein higher amounts can be given to older children.

Modified release (MR) dosage forms herein involve formulations or ingredients that modify release of gaboxadol or a pharmaceutically acceptable salt thereof into the patient. The pattern of drug release from modified release dosage forms is deliberately changed from that of a conventional dosage form to achieve a desired therapeutic objective and/or better patient compliance. MR dosage forms can make for a speedy onset of action, a slower onset of action, a delayed onset of action, a pulsed onset of action, or they can provide any combination of the foregoing. Accordingly, Types of MR dosage forms include, 1) orally disintegrating dosage forms (ODDFs) which provide immediate release, 2) extended or sustained release dosage forms, 3) delayed release dosage forms (e.g., enteric coated), 4) pulsatile release dosage forms, and 5) combinations of the foregoing. In embodiments, a combination of the foregoing can provide, e.g., both rapid release and sustained release, both rapid release and delayed release, or rapid release and sustained release which is pulsatile in nature. Accordingly, compared to conventional dosage forms, modified release dosage forms can increase or decrease absorption rates, onset of action, $C_{max}$ and/or $T_{max}$ of gaboxadol or a pharmaceutically acceptable salt thereof in the patient.

A modified release dosage form which provides rapid onset of action such as an ODDF, e.g., an orally disintegrating tablet ("ODT") or orally disintegrating film ("ODF") as described herein can advantageously release gaboxadol to the sublingual or buccal mucous membranes in the mouth (the oral mucosa) resulting in a rapid onset of action, and an earlier, $C_{max}$ and/or $T_{max}$. When gaboxadol comes into contact with the mucous membranes beneath the tongue and/or the cheek, it is absorbed directly into the bloodstream, thus bypassing the GI tract. This is because the connective tissue beneath the epithelium contains a rich network of capillaries into which the drug diffuses, thereby entering the venous circulation. In contrast, substances absorbed in the GI tract are subject to first-pass metabolism in the liver before entering the general circulation. Avoiding first pass metabolism can be preferable to conventional oral administration when rapid onset of action is desirable, since this route transports the gaboxadol directly to the brain, where it exerts it's extrasynaptic $GABA_A$ agonism.

In other clinical situations such as those where symptoms are long lasting or chronic, it may desirable to maintain a relatively constant sustained level of gaboxadol in the bloodstream leading to a sustained treatment of symptoms of 1p36 deletion syndrome. In contrast to an ODDF containing gaboxadol where onset is rapid, but duration of action is not sustained due to the short half-life of gaboxadol, a modified dosage form herein having a sustained release profile provides a sustained therapeutic level of gaboxadol which provides a prolonged period of symptom relief without the need for repeated dosing throughout the day. As discussed in more detail below certain sustained relief dosage forms are administered orally and are absorbed in the GI tract where they undergo first pass metabolism.

In embodiments, pharmaceutical ODDF compositions such as ODfs or ODTs herein provide immediate release of gaboxadol or a pharmaceutically acceptable salt thereof resulting in pharmacokinetic properties which include a $T_{max}$ of 20 minutes or less. In embodiments, pharmaceutical compositions herein provide a $T_{max}$ of 20 minutes or less, a $T_{max}$ of 19 minutes or less, a $T_{max}$ of 18 minutes or less, a $T_{max}$ of 17 minutes or less, a $T_{max}$ of 16 minutes or less, a $T_{max}$ of 15 minutes or less, a $T_{max}$ of 14 minutes or less, a $T_{max}$ of 13 minutes or less, a $T_{max}$ of 12 minutes or less, a $T_{max}$ of 11 minutes or less, a $T_{max}$ of 10 minutes or less, a $T_{max}$ of 9 minutes or less, a $T_{max}$ of 8 minutes or less, a $T_{max}$ of 7 minutes or less, a $T_{max}$ of 6 minutes or less, or a $T_{max}$ of 5 minutes or less.

ODDFs are solid dosage forms containing a medicinal substance or active ingredient which disintegrates rapidly, usually within a matter of seconds when placed upon the tongue, sublingually or buccally. The disintegration time for ODDFs generally range from one or two seconds to about a minute. ODDFs are designed to disintegrate or dissolve rapidly on contact with saliva. This mode of administration can be beneficial to people who may have problems swallowing tablets whether it be from physical infirmity or psychiatric in nature. Patients with 1p36 deletion syndrome may exhibit such behavior. In addition, ODDFs herein provide a rapid onset of action which can provide rapid alleviation or cessation of acute symptoms associated with 1p36 deletion syndrome. In embodiments, when administered to an oral cavity, an ODDF herein disintegrates in less than one minute, less than 55 seconds, less than 50 seconds, less than 45 seconds, less than 40 seconds, less than 35 seconds, less than 30 seconds, less than 25 seconds, less than 20 seconds, less than 15 seconds, less than 10 seconds, or less than 5 seconds.

An ODT is a solid dosage form containing a medicinal substance or active ingredient which disintegrates rapidly, usually within a matter of seconds when placed upon the tongue, sublingually or buccally. The disintegration time for ODTs generally ranges from several seconds to about a minute. ODTs are designed to disintegrate or dissolve rapidly on contact with saliva, thus eliminating the need to chew the tablet, swallow the intact tablet, or take the tablet with liquids. As with ODDFs in general, this mode of administration can be beneficial to people who may have problems swallowing tablets whether it be from physical infirmity or psychiatric in nature. Patients with 1p36 deletion syndrome may exhibit such behavior. In addition, ODTs herein provide a rapid onset of action which can result in a rapid alleviation or cessation of acute symptoms associated with 1p36 deletion syndrome. In embodiments, an ODT herein disintegrates in less than one minute, less than 55 seconds, less than 50 seconds, less than 45 seconds, less than 40 seconds, less than 35 seconds, less than 30 seconds, less than 25 seconds, less than 20 seconds, less than 15 seconds, less than 10 seconds, or less than 5 seconds, based upon, e.g., the United States Pharmacopeia (USP) disintegration test method set forth at section 701, Revision Bulletin Official Aug. 1, 2008.

In embodiments, the fast dissolving property of the ODTs requires quick ingress of water into the tablet matrix. This may be accomplished by maximizing the porous structure of the tablet, incorporation of suitable disintegrating agents and use of highly water-soluble excipients in the formulation. Excipients used in ODTs typically contain at least one superdisintegrant (which can have a mechanism of wicking, swelling or both), a diluent, a lubricant and optionally a swelling agent, sweeteners and flavorings. See, e.g., Nagar et al., *Journal of Applied Pharmaceutical Science*, 2011;01 (04):35-45, incorporated herein by reference. Superdisintegrants can be classified as synthetic, natural and co-processed. In this context synthetic superdisintegrants can be exemplified by sodium starch glycolate, croscarmellose sodium, cross-linked polyvinylpyrrolidone, low-substituted hydroxypropyl cellulose, microcrystalline cellulose, partially pregelatinized starch, cross-linked alginic acid and modified resin. Natural superdisintegrants can be processed mucilages and gums are obtained from plants and can be exemplified by *Lepidiurn sativurn* seed mucilage, banana powder, gellan gum, locust bean gum, xanthan gum, guar gum, gum karaya, cassia fistula seed gum, mangifera indica gum, carrageenan, agar from *Gelidium amansii and other red algaes*, soy polysaccharide and chitosan. Diluents can include, e.g., mannitol, sorbitol, xylitol, calcium carbonate, magnesium carbonate, calcium sulfate, magnesium trisilicate and the like. Lubricants can include, e.g., magnesium stearate and the like. Those skilled in the art are familiar with ODT manufacturing techniques.

Other ODDFs which may be used herein include ODFs which are thin oral strips that release medication such as gaboxadol or a pharmaceutically acceptable salt thereof quickly after administration to the oral cavity. The film is placed on a patient's tongue, sublingually, bucally, or on any other mucosal surface and is instantly wet by saliva whereupon the film rapidly hydrates and dissolves to release the medication. See. e.g., Chaturvedi et al., *Curr Drug Deliv.* 2011 Jul. 8(4):373-80. Fastcaps are a rapidly disintegrating drug delivery system based on gelatin capsules. In contrast to conventional hard gelatin capsules, fastcaps consist of a gelation of low bloom strength and various additives to improve the mechanical and dissolution properties of the capsule shell. Fastcaps are also referred to herein as orally disintegrating capsules. See, e.g., Ciper and Bodmeier, *Int J Pharm.* 2005 Oct. 13;303(1-2):62-71. Freeze dried (lyophilized) wafers (also referred to herein as orally disintegrating wafers) are rapidly disintegrating, thin matrixes that contain a medicinal agent. The wafer or film disintegrates rapidly in the oral cavity and releases drug which dissolves or disperses in the saliva. See, e.g., Boateng et al., Int J Pharm. 2010 Apr 15; 389(1-2):24-31. Those skilled in the art are familiar with various techniques utilized to manufacture ODDFs such as freeze drying, spray drying, phase transition processing, melt granulation, sublimation, mass extrusion, cotton candy processing, direct compression, etc. See, e.g., Nagar et al., supra.

When administered, ODDFs containing gaboxadol or a pharmaceutically acceptable salt thereof disintegrate rapidly to release the drug, which dissolves or disperses in the saliva. The drug may be absorbed in the oral cavity, e.g., sublingually, buccally, from the pharynx and esophagus or from other sections of gastrointestinal tract as the saliva travels down. In such cases, bioavailability can be significantly greater than that observed from conventional tablet or capsule dosage forms which travel to the stomach or intestines where drug can be released.

In embodiments, the amount of gaboxadol or pharmaceutically acceptable salt thereof within the patient about 4 hours after administration of the ODDF is between about 65% to about 85% less than the administered dose. In embodiments, the amount of gaboxadol or pharmaceutically acceptable salt thereof within the patient about 4 hours after administration of the ODDF is less than 65% 70%, 75%, 80%, or 85% of the administered dose.

In embodiments, ODDFs for treating 1p36 deletion syndrome are provided that include about 1 mg to about 50 mg of gaboxadol or a pharmaceutically acceptable salt thereof. For example, an ODDF can include 1 mg, 2 mg, 3 mg, 4 mg, 5 mg 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, or 50 mg gaboxadol or a pharmaceutically acceptable salt thereof. In embodiments, the ODDF provides improvement in symptoms of 1p36 deletion syndrome in the patient for more than 6 hours after administration of the composition to the patient.

In embodiments, relatively high doses to treat 1p36 deletion syndrome administered as a child or adult single ODDF may include amounts of gaboxadol or a pharmaceutically acceptable salt thereof in the range of about, e.g., 5 mg to 20 mg, 10 mg to 20 mg, 15 mg to 20 mg, 15 mg to 25 mg, 15 mg to 30 mg, 15 mg to 35 mg, 15 mg to 40 mg, 15 mg to 45 mg, 15 mg to 50 mg, 15 mg to 55 mg, 15 mg to 60 mg, 15 mg to 65 mg, 15 mg to 70 mg, 15 mg to 75 mg, 20 mg to 25 mg, 20 mg to 30 mg, 20 mg to 35 mg, 20 mg to 40 mg, 20 mg to 45 mg, 20 mg to 50 mg, 20 mg to 55 mg, 20 mg to 60 mg, 20 mg to 65 mg, 20 mg to 70 mg, 20 mg to 75 mg, 25 mg to 30 mg, 25 mg to 35 mg, 25 mg to 40 mg, 25 mg to 45 mg, 25 mg to 50 mg, 25 mg to 55 mg, 25 mg to 60 mg, 25 mg to 65 mg, 25 mg to 70 mg, 25 mg to 75 mg, 30 mg to 35 mg, 30 mg to 40 mg, 30 mg to 45 mg, 30 mg to 50 mg, 30 mg to 55 mg, 30 mg to 60 mg, 30 mg to 65 mg, 30 mg to 70 mg, 30 mg to 75 mg, 35 mg to 40 mg, 35 mg to 45 mg, 35 mg to 50 mg, 35 mg to 55 mg, 35 mg to 60 mg, 35 mg to 65 mg, 35 mg to 70 mg, 35 mg to 75 mg, 40 mg to 45 mg, 40 mg to 50 mg, 40 mg to 55 mg, 40 mg to 60 mg, 40 mg to 65 mg, 40 mg to 70 mg, 40 mg to 75 mg, 45 mg to 50 mg, 45 mg to 55 mg, 45 mg to 60 mg, 45 mg to 65 mg, 45 mg to 70 mg, 45 mg to 75 mg, 50 mg to 55 mg, 50 mg to 60 mg, 50 mg to 65 mg, 50 mg to 50 mg, or 50 mg to 75 mg.

Examples of relatively high child or adult single ODDF doses of gaboxadol or a pharmaceutically acceptable salt thereof to treat 1p36 deletion syndrome are 10 mg, 15 mg, 20 mg, 25 mg, 30 mg, 35 mg, 40 mg, 45 mg, 50 mg, 55 mg, 60 mg, 65 mg, 70 mg, or 75 mg.

Typically, ODDF doses of gaboxadol or a pharmaceutically acceptable salt thereof are administered once daily, twice daily or three times daily to a patient in need thereof. The methods and compositions described herein may provide reduced dosing frequency and reduced adverse events and/or increased efficacy. In embodiments, the dosage delivered by the ODDF is about, e.g., 15 mg to 225 mg/day, 20 mg to 225 mg/day, 25 mg to 225 mg/day, 30 mg to 225 mg/day, 35 mg to 225 mg/day, 40 mg to 225 mg/day, 45 mg to 225 mg/day, 50 mg to 225 mg/day, 55 mg to 225 mg/day, 60 mg to 225 mg/day, 65 mg to 225 mg/day, 70 mg to 225 mg/day, 75 mg to 225 mg/day, 80 mg to 225 mg/day, 85 mg to 225 mg/day, 90 mg to 225 mg/day, 95 mg to 225 mg/day, 100 mg to 225 mg/day, 105 mg to 225 mg/day, 110 mg to 225 mg/day, 115 mg to 225 mg/day, 120 mg to 225 mg/day, 125 mg to 225 mg/day, 130 mg to 225 mg/day, 135 mg to 225 mg/day, 140 mg to 225 mg/day, 145 mg to 225 mg/day, 150 mg to 225 mg/day, 155 mg to 225 mg/day, 160 mg to 225 mg/day, 165 mg to 225 mg/day, 170 mg to 225 mg/day, 175 mg to 225 mg/day, 180 mg to 225 mg/day, 185 mg to 225 mg/day, 190 mg to 225 mg/day, 200 mg to 225 mg/day, 205 mg to 225 mg/day, 210 mg to 225 mg/day, 215 mg to 225 mg/day, or 220 mg to 225 mg/day. For example, gaboxadol or a pharmaceutically acceptable salt thereof can be administered 15 mg/day, 20 mg/day, 25 mg/day, 30 mg/day, 35 mg/day, 40 mg/day, 45 mg/day, 50 mg/day, 55 mg/day, 60 mg/day, 65 mg/day, 70 mg/day, 75 mg/day, 80 mg/day, 85 mg/day, 90 mg/day, 100 mg/day, 105 mg/day, 115 mg/day, 120 mg/day, 125 mg/day, 130 mg/day, 135 mg/day, 140 mg/day, 145 mg/day, 150 mg/day, 155 mg/day, 160 mg/day, 165 mg/day, 170 mg/day, 1755 mg/day, 180 mg/day, 190 mg/day, 195 mg/day, 200 mg/day, 205 mg/day, 210 mg/day, 215 mg/day, 220 mg/day, or 225 mg/day. In embodiments, an ODDF including gaboxadol or a pharmaceutically acceptable salt thereof is administered at doses of 1 mg, 2 mg, 3 mg, 4 mg, 5 mg, 6 mg, 7 mg, 8 mg, 9 mg, 10 mg, 11 mg, 12 mg, 13 mg, 14 mg, 15 mg gaboxadol or a pharmaceutically acceptable salt thereof to infants with 1p36 deletion syndrome, once, twice or three times daily.

In embodiments, ODDFs herein provide an in vivo plasma profile having $C_{max}$ less than about 2500 ng/ml, 2000 ng/ml, 1750 ng/ml, 1500 ng/ml, 1250 ng/ml, 1000 ng/ml, 750 ng/ml, 500 ng/ml, 450 ng/ml, 400 ng/ml, 350 ng/ml, 300 ng/ml, 250 ng/ml, 200 ng/ml, 150 ng/ml, 100 ng/ml, 50 ng/ml or 25 ng/ml. In embodiments, ODDFs herein provide an in vivo plasma profile having a $AUC_{0-\infty}$ of less than about, e.g., 900 ng●hr/ml, 850 ng●hr/ml, 800 ng●hr/ml, 750 ng●hr/ml, or 700 ng●hr/ml 650 ng●hr/ml, 600 ng●hr/ml, 550 ng●hr/ml, 500 ng●hr/ml, or 450 ng●hr/ml. In embodiments, ODDFs herein provide an in vivo plasma profile having a $AUC_{0-\infty}$ of less than about, e.g., 400 ng●hr/ml, 350 ng●hr/ml, 300 ng●hr/ml, 250 ng●hr/ml, or 200 ng●hr/ml. In embodiments, ODDFs herein provide an in vivo plasma profile having a $AUC_{0-\infty}$ of less than about, e.g., 150 ng●hr/ml, 100 ng●hr/ml, 75 ng●hr/ml, or 50 ng●hr/ml.

In embodiments, pharmaceutical formulations having modified release profiles provide pharmacokinetic properties which result in both rapid onset and sustained duration of action. Such pharmaceutical formulations include an immediate release aspect and a sustained or extended release aspect. "Sustained" and "extended" are used interchangeably herein. Immediate release aspects are discussed above in connection with ODDFs. Extended release dosage forms (ERDFs) have an extended release profiles and are those that allow a reduction in dosing frequency as compared to that presented by a conventional dosage form, e.g., a solution or unmodified release dosage form. ERDFs provide a sustained duration of action of a drug. In embodiments, modified release dosage forms herein may incorporate an ODDF aspect to provide immediate release of a loading dose and then an ERDF aspect that provides prolonged delivery to maintain drug levels in the blood within a desired therapeutic range for a desirable period of time resulting from ingesting a unit dose of the drug. In embodiments, the ODDF aspect releases the drug immediately and the ERDF aspect thereafter provides continuous release of drug for sustained action. In embodiments, ERDFs are not combined with an ODDF aspect and can be administered as a solitary dosage form.

In embodiments, the immediate release aspect achieves a $T_{max}$ as described above. In embodiments, the extended release aspect provides an amount of gaboxadol or pharmaceutically acceptable salt thereof within the patient at about 4 or more hours after administration of the pharmaceutical formulation between about 50% to about 100% of the initially administered ODDF dose. In embodiments, the amount of gaboxadol or pharmaceutically acceptable salt thereof within the patient about 4 hours after administration of the pharmaceutical formulation is more than 50%, 55%, 60%, 65%, 70%, 75%, 80%, 85%, 90%, 95%, 100%, 105%, or 110% of the initially administered ODDF dose. In embodiments, the extended release aspect provides an amount of gaboxadol or pharmaceutically acceptable salt thereof within the patient at about 6 or more hours after administration of the pharmaceutical formulation between about 50% to about 110% of the initially administered ODDF dose. In embodiments, the amount of gaboxadol or pharmaceutically acceptable salt thereof within the patient about 6 hours after administration of the pharmaceutical formulation is more than 50%, 55%, 60%, 65%, 70%, 75%, 80%, 85%, 90%, 95%, 100%, 105%, or 110% of the initially administered ODDF dose. In embodiments, the extended release aspect provides an amount of gaboxadol or pharmaceutically acceptable salt thereof within the patient at about 8 or more hours after administration of the pharmaceutical formulation between about 50% to about 110% of the initially administered ODDF dose. In embodiments, the amount of gaboxadol or pharmaceutically acceptable salt thereof within the patient about 8 hours after administration of the pharmaceutical formulation is more than 50%, 55%, 60%, 65%, 70%, 75%, 80%, 85%, 90%, 95%, 100%, 105%, or 110% of the initially administered ODDF dose. In embodiments, the extended release aspect provides an amount of gaboxadol or pharmaceutically acceptable salt thereof within the patient at about 10 or more hours after administration of the pharmaceutical formulation between about 50% to about 110% of the initially administered ODDF dose. In embodiments, the amount of gaboxadol or pharmaceutically acceptable salt thereof within the patient about 10 hours after administration of the pharmaceutical formulation is more than 50%, 55%, 60%, 65%, 70%, 75%, 80%, 85%, 90%, 95%, 100%, 105%, or 110% of the initially administered ODDF dose. In embodiments, the extended release aspect provides an amount of gaboxadol or pharmaceutically acceptable salt thereof within the patient at about 12 or more hours after administration of the pharmaceutical formulation between about 50% to about 110% of the initially administered ODDF dose. In embodiments, the amount of gaboxadol or pharmaceutically acceptable salt thereof within the patient about 12 hours after administration of the pharmaceutical formulation is more than 50%, 55%, 60%, 65%, 70%, 75%, 80%, 85%, 90%, 95%, 100%, 105%, or 110% of the initially administered ODDF dose.

In embodiments, an ODDF is applied as a coating or band over an ERDF, or as a layer adjacent to an ERDF, to allow direct exposure of the ODDF to the oral cavity and consequent disintegration of the ODDF. In embodiments, the ODDF and the ERDF can be mixed in a chewable resin, e.g., gum. Those skilled in the art are familiar with techniques for applying coatings, bands and layers to fabricate pharmaceutical dosage forms. It should be understood that a ERDF can be administered without an ODDF aspect.

Suitable formulations which provide extended release profiles are well-known in the art. For example, coated slow release beads or granules ("beads" and "granules" are used interchangeably herein) in which, e.g., gaboxadol or a pharmaceutically acceptable salt thereof is applied to beads, e.g., confectioners nonpareil beads, and then coated with conventional release retarding materials such as waxes, enteric coatings and the like. In embodiments, beads can be formed in which gaboxadol or pharmaceutically acceptable salt thereof is mixed with a material to provide a mass from which the drug leaches out. In embodiments, the beads may be engineered to provide different rates of release by varying characteristics of the coating or mass, e.g., thickness, porosity, using different materials, etc. Beads having different rates of release may be combined into a single dosage form to provide variable or continuous release. The beads can be contained in capsules or compressed into tablets. In embodiments, the ODDF is applied as a coating, a layer or a band to a capsule or tablet. In embodiments, slow release cores which are incorporated into tablets or capsules can also provide extended release profiles. For example, gaboxadol or a pharmaceutically acceptable salt thereof can be mixed in a substance or a mixture of substances non-absorbable from the gastrointestinal tract but capable of slow dissolution or loss of drug by leaching, and an outer ODDF layer which is applied to the core by, e.g., compression or spraying. In embodiments, extended release profiles may be provided by multiple layer tablets, each layer having different release properties. Multilayer tableting machines allow incorporation into one tablet of two or more separate layers which may be made to release gaboxadol or a pharmaceutically acceptable salt thereof at different rates. For example, one or more outer layers may be an ODDF, and each other layer an ERDF that exhibits different release rates. In embodiments, gaboxadol or a pharmaceutically acceptable salt thereof is incorporated into porous inert carriers that provide extended release profiles. In embodiments, the porous inert carriers incorporate channels or passages from which the drug diffuses into surrounding fluids. In embodiments, gaboxadol or a pharmaceutically acceptable salt thereof is incorporated into an ion-exchange resin to provide an extended release profile. Prolonged action results from a predetermined rate of release of the drug from the resin when the drug-resin complex contacts gastrointestinal fluids and the ionic constituents dissolved therein. In embodiments, membranes are utilized to control rate of release from drug containing reservoirs. In embodiments, liquid preparations may also be utilized to provide an extended release profile. For example, a liquid preparation consisting of solid particles dispersed throughout a liquid phase in which the particles are not soluble. The suspension is formulated to allow at least a reduction in dosing frequency as compared to that drug presented as a conventional dosage form (e.g., as a solution or a prompt drug-releasing, conventional solid dosage form). For example, a suspension of ion-exchange resin constituents or microbeads.

In embodiments, absorbable or non-absorbable polymers may be utilized to form ERDFs. Various ERDFs including those discussed above and others that can be utilizable herein are known to those with skill in the art. See, e.g., Fu and Kao, *Expert Opin Drug Deliv.* 2010 Apr; 7(4): 429-444.

ERDFs can include relatively large amounts of gaboxadol or a pharmaceutically acceptable salt thereof since the amount of gaboxadol or a pharmaceutically acceptable salt thereof is released slowly over time. In embodiments, ERDFs for treating 1p36 deletion syndrome are provided that include about 25 mg to about 250 mg of gaboxadol or a pharmaceutically acceptable salt thereof. For example, an ERDF can include 25 mg, 30 mg, 35 mg, 40 mg, 45 mg, 50 mg, 55 mg, 60 mg, 65 mg, 70 mg, 75 mg, 80 mg, 85 mg, 90 mg, 100 mg, 105 mg, 110 mg 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg or 250 mg gaboxadol or a pharmaceutically acceptable salt thereof. In embodiments, the ERDF provides improvement in symptoms of 1p36 deletion syndrome in the patient for more than 12 hours after administration of the composition to the patient.

In embodiments, modified dosage forms herein encompass delayed release dosage forms having delayed release profiles. Delayed release dosage forms can include delayed release tablets, delayed release caplets or delayed release capsules. A delayed release tablet or caplet is a solid dosage form which releases a drug (or drugs) such as gaboxadol or a pharmaceutically acceptable salt thereof at a time other than promptly after administration. For convenience, caplets may also be referred to as tablets herein. A delayed release capsule is a solid dosage form in which the drug is enclosed within either a hard or soft soluble container made from a suitable form of gelatin, and which releases a drug (or drugs) at a time other than promptly after administration. For example, with respect to tablets or capsules, enteric-coated articles are examples of delayed release dosage forms. In embodiments, a delayed release tablet is a solid dosage form containing a conglomerate of medicinal particles that releases a drug (or drugs) at a time other than promptly after administration. In embodiments, the conglomerate of medicinal particles is covered with a coating which delays release of the drug. In embodiments, a delayed release capsule is a solid dosage form containing a conglomerate of medicinal particles that releases a drug (or drugs) at a time other than promptly after administration. In embodiments, the conglomerate of medicinal particles is covered with a coating which delays release of the drug.

In embodiments, the amount of gaboxadol or a pharmaceutically acceptable salt thereof contained in a delayed release dosage form is the same as the amounts given for conventional dosage forms. In embodiments, the amount of gaboxadol or a pharmaceutically acceptable salt thereof contained in a delayed release dosage form is the same as the amounts given for extended release dosage forms.

In embodiments, ODDFs with a delayed release formulation aspect are provided that are solid dosage forms containing medicinal substances which disintegrate rapidly, usually within a matter of seconds, when placed upon the tongue, but which also releases a drug (or drugs) at a time other than promptly after administration. Accordingly, in embodiments, modified release dosage forms herein incorporate an ODDF aspect to provide immediate release of a loading dose and then a delayed release formulation aspect that provides a period in which there is no drug delivery followed by a period of drug delivery to provide drug levels in the blood within a desired therapeutic range for a desirable period of time in excess of the activity resulting from the loading dose of the drug. In embodiments, the ODDF aspect releases the drug immediately and then, after a period of delay, a delayed release formulation aspect thereafter provides a single release of drug to provide an additional period of activity. In embodiments, the ODDF aspect releases the drug immediately and then, after a period of delay, a delayed release formulation aspect thereafter provides a continuous release of drug for sustained action.

In embodiments, the immediate release aspect of a ODDF with a delayed release aspect achieves a $T_{max}$ of 20 minutes or less, a $T_{max}$ of 19 minutes or less, a $T_{max}$ of 18 minutes or less, a $T_{max}$ of 17 minutes or less, a $T_{max}$ of 16 minutes or less, a $T_{max}$ of 15 minutes or less, a $T_{max}$ of 14 minutes or less, a $T_{max}$ of 13 minutes or less, a $T_{max}$ of 12 minutes or less, a $T_{max}$ of 11 minutes or less, a $T_{max}$ of 10 minutes or less, a $T_{max}$ of 9 minutes or less, a $T_{max}$ of 8 minutes or less, a $T_{max}$ of 7 minutes or less, a $T_{max}$ of 6 minutes or less, or a $T_{max}$ of 5 minutes or less. In embodiments, the delayed release aspect provides an amount of gaboxadol or pharmaceutically acceptable salt thereof within the patient at about 1, 2, 3 or 4 or more hours after administration of the pharmaceutical formulation between about 50% to about 110% of the initially administered ODDF dose. In embodiments, the amount of gaboxadol or pharmaceutically acceptable salt thereof within the patient about 1, 2, 3 or 4 hours after administration of the pharmaceutical formulation is more than 50%, 55%, 60%, 65%, 70%, 75%, 80%, 85%, 90%, 95%, 100%, 105%, or 110% of the initially administered ODDF dose. In embodiments, the delayed release formulation aspect provides an amount of gaboxadol or pharmaceutically acceptable salt thereof within the patient at about 6 or more hours after administration of the pharmaceutical formulation between about 50% to about 110% of the initially administered ODDF dose. In embodiments, the amount of gaboxadol or pharmaceutically acceptable salt thereof within the patient about 6 hours after administration of the pharmaceutical formulation is more than 50%, 55%, 60%, 65%, 70%, 75%, 80%, 85%, 90%, 95%, 100%, 105%, or 110% of the initially administered ODDF dose. In embodiments, the delayed release formulation aspect provides an amount of gaboxadol or pharmaceutically acceptable salt thereof within the patient at about 8 or more hours after administration of the pharmaceutical formulation between about 50% to about 110% of the initially administered ODDF dose. In embodiments, the amount of gaboxadol or pharmaceutically acceptable salt thereof within the patient about 8 hours after administration of the pharmaceutical formulation is more than 50%, 55%, 60%, 65%, 70%, 75%, 80%, 85%, 90%, 95%, 100%, 105%, or 110% of the initially administered ODDF dose. In embodiments, the delayed release formulation aspect provides an amount of gaboxadol or pharmaceutically acceptable salt thereof within the patient at about 10 or more hours after administration of the pharmaceutical formulation between about 50% to about 110% of the initially administered ODDF dose. In embodiments, the amount of gaboxadol or pharmaceutically acceptable salt thereof within the patient about 10 hours after administration of the pharmaceutical formulation is more than 50%, 55%, 60%, 65%, 70%, 75%, 80%, 85%, 90%, 95%, 100%, 105%, or 110% of the initially administered ODDF dose. In embodiments, the delayed release formulation aspect provides an amount of gaboxadol or pharmaceutically acceptable salt thereof within the patient at about 12 or more hours after administration of the pharmaceutical formulation between about 50% to about 110% of the initially administered ODDF dose. In embodiments, the amount of gaboxadol or pharmaceutically acceptable salt thereof within the patient about 12 hours after administration of the pharmaceutical formulation is more than 50%, 55%, 60%, 65%, 70%, 75%, 80%, 85%, 90%, 95%, 100%, 105%, or 110% of the initially administered ODDF dose.

Delayed release dosage forms are known to those skilled in the art. For example, coated delayed release beads or granules ("beads" and "granules" are used interchangeably herein) in which, e.g., gaboxadol or a pharmaceutically acceptable salt thereof is applied to beads, e.g., confectioners nonpareil beads, and then coated with conventional release delaying materials such as waxes, enteric coatings and the like. In embodiments, beads can be formed in which gaboxadol or pharmaceutically acceptable salt thereof is mixed with a material to provide a mass from which the drug leaches out. In embodiments, the beads may be engineered to provide different rates of release by varying characteristics of the coating or mass, e.g., thickness, porosity, using different materials, etc. In embodiments, enteric coated granules of gaboxadol or a pharmaceutically acceptable salt thereof can be contained in an enterically coated capsule or tablet which releases the granules in the small intestine. In embodiments, the granules have a coating which remains intact until the coated granules reach at least the ileum and thereafter provide a delayed release of the drug in the colon. Suitable enteric coating materials are well known in the art, e.g., Eudragit® coatings such methacrylic acid and methyl methacrylate polymers and others. The granules can be contained in capsules or compressed into tablets. In embodiments, the ODDF is applied as a coating, a layer or a band to the capsule or tablet. In embodiments, delayed release cores which are incorporated into tablets or capsules can also provide delayed release profiles. For example, gaboxadol or a pharmaceutically acceptable salt thereof can be mixed in a substance or a mixture of substances non-absorbable from the gastrointestinal tract but capable of slow dissolution or loss of drug by leaching, and an outer ODDF layer which is applied to the core by, e.g., compression or spraying. In embodiments, delayed release profiles may be provided by multiple layer tablets, each layer having different release properties. Multilayer tableting machines allow incorporation into one tablet of two or more separate layers which may be made to release gaboxadol or a pharmaceutically acceptable salt thereof at different rates after a period of delay. For example, one or more outer layers may be an ODDF, and each other layer a delayed release dosage form that exhibits different release rates. In embodiments, gaboxadol or a pharmaceutically acceptable salt thereof is incorporated into porous inert carriers that provide delayed release profiles. In embodiments, the porous inert carriers incorporate channels or passages from which the drug diffuses into surrounding fluids. In embodiments, gaboxadol or a pharmaceutically acceptable salt thereof is incorporated into an ion-exchange resin to provide a delayed release profile. Delayed action may result from a predetermined rate of release of the drug from the resin when the drug-resin complex contacts gastrointestinal fluids and the ionic constituents dissolved therein. In embodiments, membranes are utilized to control rate of release from drug containing reservoirs. In embodiments, liquid preparations may also be utilized to provide a delayed release profile. For example, a liquid preparation consisting of solid particles dispersed throughout a liquid phase in which the particles are not soluble. The suspension is formulated to allow at least a reduction in dosing frequency as compared to that drug presented as a conventional dosage form (e.g., as a solution or a prompt drug-releasing, conventional solid dosage form). For example, a suspension of ion-exchange resin constituents or microbeads.

In embodiments, an ODDF is applied as a coating or band over a delayed release dosage form, or as a layer adjacent to a delayed release dosage form, to allow direct exposure of the ODDF to the oral cavity and consequent disintegration of the ODDF. In embodiments, the ODDF and a delayed release dosage form can be mixed in a chewable resin, e.g., gum. Those skilled in the art are familiar with techniques for applying coatings, bands and layers to fabricate pharmaceutical dosage forms.

In embodiments, modified release pharmaceutical formulations herein include pulsatile release dosage formulations (PRDFs). Pulsatile drug release involves rapid release of defined or discrete amounts of a drug (or drugs) such as gaboxadol or a pharmaceutically acceptable salt thereof after a lag time following an initial release of a loading amount of drug. In embodiments, PRDFs can provide a single pulse. In embodiments, PRDFs can provide multiple pulses over time. Various PRDFs are known to those with skill in the art.

In embodiments, a PRDF can be a capsule. In embodiments, release after a lag time is provided by a system that uses osmotic pressure to cause release of a plug. In this system, gaboxadol or a pharmaceutically acceptable salt thereof is contained in an insoluble capsule shell sealed by an osmotically responsive plug, e.g., a hydrogel, which is pushed away by swelling or erosion. When the seal is broken the drug is released as a pulse from the capsule body. Contact with gastrointestinal fluid or dissolution medium causes the plug to swell, either pushing itself out of the capsule or causing the capsule to rupture after the lag-time. Position & dimensions of the plug can control lag-time. For rapid release of drug effervescent or disintegrating agents may be added. Effervescent materials can cause an increase in pressure thus aiding or causing expulsion of the plug. Examples of suitable plug material may be swellable materials coated with permeable polymer (polymethacrylates), erodible compressed polymer (HPMC, polyvinyl alcohol), congealed melted polymer (glyceryl monooleate), and enzymatically controlled erodible polymers such as pectin. In embodiments, an insoluble capsule contains multiple drug compartments separated by osmotically activated plugs. When a first plug is exposed to the environmental fluids, the first compartment opens, drug is released, and the adjacent plug is exposed. The process continues until no sealed compartments are left. Lag time between pulses can be further controlled by varying the thickness of the plug and the properties of the materials from which the plug is made. More hygroscopic materials will absorb fluid faster and will swell faster. In embodiments, a membrane may be substituted for the plug. If effervescent materials are included in one or more compartments, fluids pass through the membrane by osmosis and the effervescent action and pressure increase causes the membrane to rupture, thereby releasing the drug. In embodiments, the membrane(s) are erodible and dissolve to release the contents of the compartment(s). Varying the thickness, porosity and properties of materials of the membrane can allow further control of lag time between pulses. In embodiments, a PRDF can be a tablet. In embodiments, single pulse tablets involve a core containing gaboxadol or a pharmaceutically acceptable salt thereof surrounded by one or more layers of swellable, rupturable coatings. In embodiments, a rupturable coating surrounds a swellable layer. As the swellable layer expands, it causes the rupturable coating to rupture, thereby releasing the drug from the core. Swellable materials such as hydrogels are well known. In embodiments, an inner swelling layer can contain a superdisintegrant, e.g., croscarmellose sodium, and an outer rupturable layer can be made of a polymeric porous material such as polyethylene oxides, ethylcellulose and the like. Porous film coats of sucrose may also be suitable. In embodiments, multiple pulse tablets incorporate multiple layers surrounding a core. As a first outermost layer erodes and releases the drug contained within the layer, an underlying layer is exposed, thus releasing drug after a predetermined lag time. The process repeats until the innermost core is exposed.

The amount of gaboxadol or a pharmaceutically acceptable salt thereof contained in or delivered by a PRDF can be the same as the amounts given for conventional dosage forms or EDRFs.

In embodiments, PRDFs can incorporate ODDFs that are solid dosage forms containing medicinal substances which disintegrate rapidly, usually within a matter of seconds, when placed upon the tongue, but which also releases a drug (or drugs) in pulsatile fashion. Accordingly, in embodiments, modified release dosage forms herein incorporate an ODDF aspect to provide immediate release of a loading dose and a PRDF aspect that provides a period in which there is no drug delivery (lag time) followed by pulsatile drug delivery to provide drug levels in the blood within a desired therapeutic range for a desirable period of time in excess of the activity resulting from a single loading dose of the drug. In embodiments, the ODDF aspect releases the drug immediately and then, after a period of delay, the PRDF aspect thereafter provides a single pulse release of drug to provide an additional period of activity. In embodiments, the ODDF aspect releases the drug immediately and then, after a period of delay, the PRFD aspect thereafter provides multiple pulsatile release of drug for prolonged therapeutic effect.

In embodiments, the immediate release aspect of a ODDF with a PRDF aspect achieves a $T_{max}$ of 20 minutes or less, a $T_{max}$ of 19 minutes or less, a $T_{max}$ of 18 minutes or less, a $T_{max}$ of 17 minutes or less, a $T_{max}$ of 16 minutes or less, a $T_{max}$ of 15 minutes or less, a $T_{max}$ of 14 minutes or less, a $T_{max}$ of 13 minutes or less, a $T_{max}$ of 12 minutes or less, a $T_{max}$ of 11 minutes or less, a $T_{max}$ of 10 minutes or less, a $T_{max}$ of 9 minutes or less, a $T_{max}$ of 8 minutes or less, a $T_{max}$ of 7 minutes or less, a $T_{max}$ of 6 minutes or less, or a $T_{max}$ of 5 minutes or less. In embodiments, a PRDF aspect provides an amount of gaboxadol or pharmaceutically acceptable salt thereof within the patient at about 0.5, 1, 2, 3 or 4 or more hours after administration of the pharmaceutical formulation between about 50% to about 110% of the initially administered ODDF dose. In embodiments, the amount of gaboxadol or pharmaceutically acceptable salt thereof within the patient about 0.5, 1, 2, 3 or 4 hours after administration of the pharmaceutical formulation is more than 50%, 55%, 60%, 65%, 70%, 75%, 80%, 85%, 90%, 95%, 100%, 105%, or 110% of the initially administered ODDF dose. In embodiments, a PRDF aspect provides an amount of gaboxadol or pharmaceutically acceptable salt thereof within the patient at about 6 or more hours after administration of the pharmaceutical formulation between about 50% to about 110% of the initially administered ODDF dose. In embodiments, the amount of gaboxadol or pharmaceutically acceptable salt thereof within the patient about 6 hours after administration of the pharmaceutical formulation is more than 50%, 55%, 60%, 65%, 70%, 75%, 80%, 85%, 90%, 95%, 100%, 105%, or 110% of the initially administered ODDF dose. In embodiments, a PRDF aspect provides an amount of gaboxadol or pharmaceutically acceptable salt thereof within the patient at about 8 or more hours after administration of the pharmaceutical formulation between about 50% to about 110% of the initially administered ODDF dose. In embodiments, the amount of gaboxadol or pharmaceutically acceptable salt thereof within the patient about 8 hours after administration of the pharmaceutical formulation is more than 50%, 55%, 60%, 65%, 70%, 75%, 80%, 85%, 90%, 95%, 100%, 105%, or 110% of the initially administered ODDF dose. In embodiments, a PRDF aspect provides an amount of gaboxadol or pharmaceutically acceptable salt thereof within the patient at about 10 or more hours after administration of the pharmaceutical formulation between about 50% to about 110% of the initially administered ODDF dose. In embodiments, the amount of gaboxadol or pharmaceutically acceptable salt thereof within the patient about 10 hours after administration of the pharmaceutical formulation is more than 50%, 55%, 60%, 65%, 70%, 75%, 80%, 85%, 90%, 95%, 100%, 105%, or 110% of the initially administered ODDF dose. In embodiments, a PRDF aspect provides an amount of gaboxadol or pharmaceutically acceptable salt thereof within the patient at about 12 or more hours after administration of the pharmaceutical formulation between about 50% to about 110% of the initially administered ODDF dose. In embodiments, the amount of gaboxadol or pharmaceutically acceptable salt thereof within the patient about 12 hours after administration of the pharmaceutical formulation is more than 50%, 55%, 60%, 65%, 70%, 75%, 80%, 85%, 90%, 95%, 100%, 105%, or 110% of the initially administered ODDF dose. In embodiments, the PRDF delivers one pulse in accordance with the above amounts. In embodiments, the PRDF delivers two pulses in accordance with the above amounts. In embodiments, the PRDF delivers three pulses in accordance with the above amounts. In embodiments, the PRDF delivers four pulses in accordance with the above amounts. In embodiments, the PRDF delivers five pulses in accordance with the above amounts. In embodiments, the PRDF delivers six pulses in accordance with the above amounts. In embodiments, the PRDF delivers seven pulses in accordance with the above amounts. In embodiments, the PRDF delivers eight pulses in accordance with the above amounts. In embodiments, the PRDF delivers nine pulses in accordance with the above amounts. The pulses may be provided in intervals separated by 0.25 h, 0.5 h, 0.75 h, 1 h, 1.25 h, 1.5 h, 1.75 h, 2 h, 2.25 h, 2.5 h, 2.75 h, 3 h, 3.25 h, 3.5 h, 3.75 h, 4 h, 4.25 h, 4.5 h, 4.75 h, 5 h, 5.5 h, 6 h, 7 h, 8 h, 9 h, 10 h, 11 h, or 12 h. In embodiments the amount of gaboxadol or a pharmaceutically acceptable salt thereof released with each pulse may vary.

In embodiments, an ODDF is applied as a coating or band over a PRDF, or as a layer adjacent to a PRDF, to allow direct exposure of the ODDF to the oral cavity and consequent disintegration of the ODDF. In embodiments, the ODDF and a PRDF can be mixed in a chewable resin, e.g., gum. Those skilled in the art are familiar with techniques for applying coatings, bands and layers to fabricate pharmaceutical dosage forms.

In embodiments, a modified release dosage form includes a transdermal dosage form. Transdermal delivery of gaboxadol as described herein can provide sustained release profiles while avoiding first pass metabolism. Transdermal delivery is a painless method of delivering gaboxadol systemically by applying a formulation containing gaboxadol onto intact and healthy skin. The drug initially penetrates through the stratum corneum and then passes through the deeper epidermis. When the gaboxadol reaches the dermal layer, it becomes available for systemic absorption via dermal microcirculation. Transdermal delivery may have certain advantages over other routes of drug delivery. It can provide a non-invasive alternative to parenteral routes, thus circumventing issues such as needle phobia. A large surface area of skin and ease of access allows many placement options on the skin for transdermal absorption. Furthermore, the pharmacokinetic profile of transdermally administered gaboxadol may be more uniform with fewer peaks, thus minimizing the risk of toxic side effects. As with sustained release dosage forms, transdermal delivery can improve patient compliance due to the reduction of dosing frequencies and is also suitable for patients who are unconscious or vomiting, or those who rely on self-administration.

Transdermal formulations may encompass dosage forms of gels, ointments, lotions, sprays, or patches. Transdermal formulations such as patches rely for their effect, on delivery of a known flux of drug to the skin for a prolonged period of time, generally a day, several days, or a week. Two mechanisms may be used to regulate drug flux: either the drug is contained within a drug reservoir, which is separated from the skin of the wearer by a synthetic membrane, through which the drug diffuses; or the drug is held dissolved or suspended in a polymer matrix, through which the drug diffuses to the skin. In embodiments, transdermal pharmaceutical formulations herein are formulated to provide maximum thermodynamic driving force for passive diffusion across the skin which is saturated with sufficient payload of gaboxadol to insure delivery across the skin. In delivery systems involving transdermal patches, gaboxadol, e.g., gaboxadol monohydrate or gaboxadol hydrochloride is stored, e.g., in a reservoir (reservoir type) or dissolved in a liquid or gel-based reservoir (matrix type).

The amount of gaboxadol or a pharmaceutically acceptable salt thereof contained in or delivered by transdermal pharmaceutical formulations herein can be the same as the amounts given for conventional dosage forms or EDRFs.

In embodiments, transdermal formulations may include chemical penetration enhancers and emulsions to facilitate transport of gaboxadol across the statum corneum. Examples of suitable penetration enhancers are alcohols, sulphoxides, azone, pyrrolidones, essential oils, terpenes and terpenoids, fatty acids, water and urea. In embodiments, semisolid vehicles such as proniosomes and microemulsion gels may be utilized as penetration enhancers. Proniosomes are non-ionic based surfactant vesicles, and may be known as "dry niosomes" since they can require hydration before drug release and permeation through the skin. Upon hydration proniosomes are converted into niosomes which are capable of diffusing across the stratum corneum and then adhere to the cell surface which causes a high thermodynamic activity gradient of the drug at the vesicle/stratum corneum surface, thus acting as the driving force for the penetration of drugs across the skin.

The starting point for the evaluation of the kinetics of drug release from a transdermal patch is an estimation of the drug compound's maximum flux across the skin (flux (J)) which is typically expressed in units of $\mu g/cm^2/h$). Based on Fick's law of diffusion, the transport of gaboxadol molecules across skin will be maintained until the concentration gradient ceases to exist.

Accordingly, transdermal pharmaceutical formulations incorporating a reservoir will deliver a steady flux of gaboxadol across the membrane as long as excess undissolved drug remains in the reservoir. The time required for gaboxadol to reach a steady state of diffusion is called the lag time. In embodiments, matrix or monolithic devices may be characterized by a falling drug flux with time, as the matrix layers closer to the skin are depleted of drug. In embodiments, reservoir patches can include a porous membrane covering the reservoir of medication which can control release, while heat melting thin layers of medication embedded in the polymer matrix (e.g., the adhesive layer), can control release of drug from matrix or monolithic devices.

In embodiments, transdermal patches can include a release liner which protects the patch during storage and is removed prior to use, drug or drug solution in direct contact with the release liner, an adhesive which serves to adhere the components of the patch together along with adhering the patch to the skin, one or more membranes which can separate other layers, control the release of the drug from the reservoir and multi-layer patches, etc., and backing which protects the patch from the outer environment.

In embodiments, transdermal patches may include, but are not limited to, single-layer drug-in-adhesive patches, wherein the adhesive layer contains gaboxadol and serves to adhere the various layers of the patch together, along with the entire patch system to the skin, but is also responsible for the releasing of the drug; multi-layer drug-in-adhesive, wherein which is similar to a single-layer drug-in-adhesive patch, but contains multiple layers, for example, a layer for immediate release of the drug and another layer for controlled release of drug from the reservoir; reservoir patches wherein the drug layer is a liquid compartment containing a drug solution or suspension separated by the adhesive layer; matrix patches, wherein a drug layer of a semisolid matrix containing a drug solution or suspension which is surrounded and partially overlaid by the adhesive layer; and vapor patches, wherein an adhesive layer not only serves to adhere the various layers together but also to release vapor. Methods for making transdermal patches are described, e.g., in U.S. Pat. Nos. 6,461,644, 6,676,961, 5,985,311, and 5,948,433.

For example, an exemplary patch can include an impermeable backing bonded about its periphery to a permeation enhancer release rate controlling element and spaced apart therefrom in its central portion to define a permeation enhancer reservoir. The permeation enhancer release rate controlling element is similarly bonded about its periphery to a porous support member and spaced apart therefrom in its central portion to define an aqueous drug reservoir containing gaboxadol, which is water soluble. A contact adhesive layer which is permeable to the gaboxadol and enhancer can be bonded to the surface of porous support and a strippable release liner, adapted to protect the adhesive prior to use and can be readily removed therefrom, may also be provided. To permit transport of drug and enhancer to the skin, the adhesive may be porous or hydrated to be permeable to the drug and enhancer. If impermeable to drug and enhancer, the adhesive can be located or otherwise adapted to impose no significant resistance to drug and permeation enhancer transport to the skin. In embodiments, a porous polyacrylate adhesive can be utilized in the contact adhesive layer. If a hydratable contact adhesive formulation is used, the adhesive can be equilibrated with at least about 10 weight percent water to permit transport of ionized drug. It should be recognized, however, that if a peripherally located adhesive is used, it need not be porous or permeable. Also, if desired, an adhesive overlay or some other means such as buckles, belts, or elastic bands could be used to maintain the transdermal delivery device on the skin in which case, if properly packaged, the adhesive layer and the strippable release liner could be omitted. Such a system might be desirable, for example, if the drug adversely affected the adhesive properties of the adhesive layer or if the drug were highly soluble in the adhesive.

In embodiments, the aqueous reservoir containing the gaboxadol dispersed therein can contain at least 50%, e.g., 55%, 60%, 65%, 70%, 75%, 80%, 85% or 90%, water. In embodiments, the gaboxadol is present at a level above saturation. In embodiments, the reservoir can be in the form of a gel which may also contain stabilizing agents, other excipients and additives. A buffering agent may also be present if required to maintain the drug reservoir at physiological pH.

The permeation enhancer release rate controlling membrane controls the rate of release of the permeation enhancer from the permeation enhancer reservoir to the skin. In embodiments, a porous substrate functions as a physical support for the gelled aqueous reservoir and it should be sufficiently porous so that it imposes little or no resistance to the transport of drug and permeation enhancer to the skin. In this regard, viscosity of the aqueous reservoir can be related to the porosity of the porous substrate, i.e., it should be sufficiently viscous so that the aqueous reservoir will not readily flow through the porous substrate. The amount of gelling or other thickening agent used is not critical but should be an amount required to produce a viscosity in the aqueous reservoir sufficient to prevent the reservoir from migrating or otherwise leaking or oozing through the porous substrate. The porous adhesive is likewise selected to provide little or no resistance to drug or enhancer release. A function of the porous substrate is to provide a support to which the adhesive can be applied since it is difficult in many cases to provide a good bond between the porous adhesive and the aqueous medium within the reservoir. In embodiments, the rate controlling membrane can be a hydrophobic membrane which is capable of controlling the rate of release of the permeation enhancer from the enhancer reservoir while simultaneously preventing either water or the drug from diffusing or otherwise migrating into enhancer reservoir. In embodiments, upon standing, the aqueous drug reservoir can contain a saturation level of the permeation enhancer.

The impermeable backing can be any material which has the desired flexibility, impermeability and insolubility with respect to the permeation enhancer and may, e.g., either be a single element or a metalized or composite coated element. Suitable materials can include, without limitation, ethylene vinyl acetate copolymers (EVA), polyesters, metalized polyesters, polyethylenes, polycarbonates, polyvinyl chlorides, polyvinylidene fluoride, polysulfones, or laminates of the above such as metalized polyester/EVA or medium density polyethylene/EVA.

In embodiments, the porous substrate can be a soft, open-mesh, hydrophobic, fibrous material or may also be a non-fibrous, porous or sponge-like material as long as the substrate performs the function of being bondable to the adhesive and maintaining the gelled aqueous material within the reservoir without providing any significant resistance to the transport of drug and permeation enhancer. Examples of suitable materials include spun laced polyester, spun-laced polyolefin coated polyester, spun bonded polyethylene, spun laced polyethylene or EVA, microporous polypropylene, microporous polycarbonate, woven nylon, rayon or polyester cloths, and open cellular polyethylene or polyurethane foams.

The porous adhesive can be, e.g., a polyacrylate contact adhesive or any other suitable porous adhesive. Alternatively, the adhesive can be a non-porous contact adhesive which is applied about the periphery leaving the center portion beneath the aqueous reservoir substantially free of adhesive. In that case, any biocompatible contact adhesive could be applied, porous or not. Examples of adhesive compositions include silicone adhesives, polyacrylates, polyisobutylene-mineral oil adhesives, tackified styrene-isoprene-styrene block copolymers (SIS), tackified EVA contact adhesives, polyacrylamides and various hydratable, hot melt or emulsified (water borne) adhesive compositions.

The strippable release liner can be any material known to the art and may be the same as or different from the material used to provide the impermeable backing. A basic requirement for the strippable release liner is that it be substantially impermeable to the passage of components from the reservoir and be readily removed from the adhesive without destruction of the integrity of the patch.

With respect to the gelled aqueous drug reservoir, in the case of gaboxadol it is intended that water be the continuous phase. For that reason, the reservoir should be at least 50%, e.g., over 70% water. The gelling agent used to thicken the reservoir can be any of a wide variety of gelling agents, such as silica, particulate porous polyisoprene, bentonite clay, various gums such as agar, tragacanth, polysaccharides, cellulosic materials such as hydroxyethyl cellulose, hydroxypropyl cellulose or hydroxypropyl methyl cellulose and polyacrylates. The basic requirements are that the gelling agent is non-reactive with gaboxadol and does not substantially interfere with the ready diffusion of the materials from the patch. A relatively wide degree of flexibility in the amount of gelling agent used is available since the required viscosity varies inversely with the pore size selected for the substrate. A general range of approximately 1% to 10% by weight of these gelling agents may be adequate.

The drug reservoir may also contain a buffer to maintain the pH of the solution in a desired range during the drug delivery period. Suitable buffers should, of course, be unreactive with the other components of the system. Suitable buffers for acid drugs and basic drugs include, without limitation, phosphates, citrates, ascorbates and carbonates.

The permeation enhancer release rate controlling membrane should be substantially impermeable to the flow of water and gaboxadol from the aqueous reservoir into the permeation enhancer reservoir while having a sufficient degree of permeability to the permeation enhancer to permit the rate at which the permeation enhancer is released from the permeation enhancer reservoir into the skin to be controlled by membranes of reasonable thickness, e.g., in the range of 0.001-0.003 inches. The permeation enhancer release rate controlling membrane may either be a solid membrane or a microporous membrane having rate controlling material in the micropores to meter the release of permeation enhancer. Examples of rate controlling materials for the formation of a membrane per se or for the rate controlling material to be included in the pores of a microporous membrane can be, e.g., hydrophobic materials such as polyethylene EVA, polycarbonates, polyvinyl chloride, polyacrylate polymers, polysulfone polymers, polyvinylidienes, polyvinylidenes, polyesters, and polyisobutylenes.

The permeation enhancer may be present in the permeation enhancer reservoir either neat or as solution or dispersion in an appropriate medium. Exemplary materials include surfactants, such as alkyl substituted sulfoxides, e.g., n-octyl methyl sulfoxide, n-nonyl methyl sulfoxide, n-decylmethyl sulfoxide (n-DMS), n-undecyl methyl sulfoxide, n-dodecyl methyl sulfoxide; mono- and di-substituted alkyl polyethylene glycols such as polyethylene glycol mono laurate and polyethylene glycol di laurate; ethanol and other lower alcohols; n-methyl pyrrolidone, dimethyl lauramine, diethyltoluamide, and the 1-substituted azacycloalkan-2-ones.

In embodiments, active methods are utilized to drive penetration of gaboxadol through the stratum corneum. In embodiments, active methods for skin permeabilisation involve the use of external energy to act as a driving force for drug transport across the skin or by physically disrupting the stratum corneum. Active methods for skin permeabilisation include ultrasound, electrically assisted methods (electroporation and iontophoresis), velocity based devices (powder injection, jet injectors), thermal approaches (lasers and radio-frequency heating) and mechanical methodologies such as microneedles and tape stripping.

In embodiments, a patient with 1p36 deletion syndrome and in need of treatment thereof is administered a either a conventional release composition, a modified release pharmaceutical composition, e.g., an ODDF, a ERDF, a DRDF, a PRDF or a transdermal pharmaceutical formulation including gaboxadol or a pharmaceutically acceptable salt thereof. Gaboxadol or pharmaceutically acceptable salt thereof may be provided as an acid addition salt, a zwitter ion hydrate, zwitter ion anhydrate, hydrochloride or hydrobromide salt, or in the form of the zwitter ion monohydrate. Acid addition salts, include but are not limited to, maleic, fumaric, benzoic, ascorbic, succinic, oxalic, bis-methylenesalicylic, methanesulfonic, ethane-disulfonic, acetic, propionic, tartaric, salicylic, citric, gluconic, lactic, malic, mandelic, cinnamic, citraconic, aspartic, stearic, palmitic, itaconic, glycolic, p-amino-benzoic, glutamic, benzene sulfonic or theophylline acetic acid addition salts, as well as the 8-halotheophyllines, for example 8-bromo-theophylline. In other suitable embodiments, inorganic acid addition salts, including but not limited to, hydrochloric, hydrobromic, sulfuric, sulfamic, phosphoric or nitric acid addition salts may be used.

In embodiments, gaboxadol is provided as gaboxadol monohydrate. One skilled in the art will readily understand that the amounts of active ingredient in a pharmaceutical formulation will depend on the form of gaboxadol provided. For example, pharmaceutical formulations including 5.0, 10.0, or 15.0 mg gaboxadol correspond to 5.6, 11.3, or 16.9 mg gaboxadol monohydrate.

In embodiments, gaboxadol is crystalline, such as the crystalline hydrochloric acid salt, the crystalline hydrobromic acid salt, or the crystalline zwitter ion monohydrate. In embodiments, gaboxadol is provided as a crystalline monohydrate.

In embodiments methods of treating a patient with 1p36 deletion syndrome include administering to a patient in need thereof a conventional release composition or a modified release pharmaceutical formulation including about 0.05 mg to about 250 mg gaboxadol or a pharmaceutically acceptable salt thereof. As mentioned above, conventional release compositions include compositions for parenteral administration. Examples of parenteral modes of administration include intravenous, intraperitoneal, intrathecal, intramuscular and subcutaneous modes of administration.

In embodiments, pharmaceutical compositions for parenteral administration are provided wherein the pharmaceutical composition remains soluble. In embodiments, pharmaceutical compositions for parenteral administration are provided that are stable, soluble, local site compatible and/or ready-to-use. In embodiments, pharmaceutical compositions for parenteral administration are aqueous compositions. In embodiments, pharmaceutical compositions for parenteral administration are suspensions. In embodiments, pharmaceutical compositions for parenteral administration are emulsions. In embodiments, the pharmaceutical compositions herein are ready-to-use for direct administration to a patient in need thereof.

The amount of gaboxadol or a pharmaceutically acceptable salt thereof contained in or delivered by parenteral pharmaceutical formulations herein can be the same as the amounts given for conventional dosage forms or ODDFs.

In embodiments, parenteral pharmaceutical compositions including gaboxadol or a pharmaceutically acceptable salt thereof are provided wherein the gaboxadol or pharmaceutically acceptable salt thereof is present at a molarity less than about 1.0 M. In embodiments, gaboxadol or pharmaceutically acceptable salt thereof is present at a molarity greater than, e.g., about 0.0001 M about 0.001 M, about 0.01 M, about 0.1 M, about 0.2 M, greater than about 0.5, greater than about 1.0 M, greater than about 1.2 M, greater than about 1.5 M, greater than about 1.75 M, greater than about 2.0 M, or greater than about 2.5 M. In embodiments, gaboxadol or pharmaceutically acceptable salt thereof is present at a molarity of between, e.g., about 0.00001 M to about 0.1 M, about 0.01 to about 0.1 M, about 0.1 M to about 1.0 M, about 1.0 M to about 5.0 M, or about 5.0 M to about 10.0 M. In embodiments, gaboxadol or pharmaceutically acceptable salt thereof is present at a molarity of less than, e.g., about 0.01 M, about 0.1 M, about 1.0 M, about 5.0 M, or about 10.0 M.

The pharmaceutical compositions for parenteral administration provided herein may include one or more excipients, e.g., solvents, solubility enhancers, suspending agents, buffering agents, isotonicity agents, stabilizers or antimicrobial preservatives. When used, the excipients of the parenteral compositions will not adversely affect the stability, bioavailability, safety, and/or efficacy of gaboxadol or a pharmaceutically acceptable salt thereof used in the composition. Thus, parenteral compositions are provided wherein there is no incompatibility between any of the components of the dosage form.

In embodiments, the solubility of gaboxadol or pharmaceutically acceptable salt thereof in the parenteral composition is greater than, e.g., about 10 mg/mL, about 15 mg/mL, about 20 mg/mL, about 25 mg/mL, about 30 mg/mL, about 40 mg/mL, about 50 mg/mL, about 75 mg/mL, about 100 mg/mL, about 150 mg/mL, when measured, for example, in water at 25° C.

In embodiments, parenteral compositions including gaboxadol or a pharmaceutically acceptable salt thereof include a stabilizing amount of at least one excipient. For example, excipients may be selected from the group consisting of buffering agents, solubilizing agents, tonicity agents, antioxidants, chelating agents, antimicrobial agents, and preservative. One skilled in the art will appreciate that an excipient may have more than one function and be classified in one or more defined group.

In embodiments, parenteral compositions include gaboxadol or a pharmaceutically acceptable salt thereof and an excipient wherein the excipient is present at a weight percent (w/v) of less than about, e.g., 10%, 5%, 2.5%, 1%, or 0.5%. In embodiments, the excipient is present at a weight percent between about, e.g., 1.0% to 10%, 10% to 25%, 15% to 35%, 0.5% to 5%, 0.001% to 1%, 0.01% to 1%, 0.1% to 1%, or 0.5% to 1%. In embodiments, the excipient is present at a weight percent between about, e.g., 0.001% to 1%, 0.01% to 1%, 1.0% to 5%, 10% to 15%, or 1% to 15%.

In embodiments, parenteral pharmaceutical compositions are provided including gaboxadol, or a pharmaceutically acceptable salt thereof and an excipient wherein the excipient comprises a stabilizing amount of a buffering agent. In embodiments, the buffering agent can be a citrate, phosphate, acetate, tartrate, carbonate, glutamate, lactate, succinate, bicarbonate buffer and combinations thereof. For example, sodium citrate, trisodium citrate anhydrous, trisodium citrate dihydrate, sodium citrate dehydrate, triethanolamine (TRIS), trisodium citrate pentahydrate dihydrate (i.e., trisodium citrate dehydrate), acetic acid, citric acid, glutamic acid, phosphoric acid, may be used as a buffering agent. In embodiments, the buffering agent may be an amino acid, alkali metal, or alkaline earth metal buffer. For example, the buffering agent may be sodium acetate or hydrogen phosphate.

In embodiments, parenteral compositions containing gaboxadol or a pharmaceutically acceptable salt thereof are provided, wherein the pH of the composition is between about 4.0 to about 8.0. In embodiments, the pH of the compositions is between, e.g., about 5.0 to about 8.0, about 6.0 to about 8.0, about 6.5 to about 8.0. In embodiments, the pH of the compositions is between, e.g., about 6.5 to about 7.5, about 7.0 to about 7.8, about 7.2 to about 7.8, or about 7.3 to about 7.6. In embodiments, the pH of the aqueous solution is, e.g., about 6.8, about 7.0, about 7.2, about 7.4, about 7.6, about 7.7, about 7.8, about 8.0, about 8.2, about 8.4, or about 8.6 are provided, wherein the pH of the composition is between about 4.0 to about 8.0. In embodiments, the pH of the compositions is between, e.g., about 5.0 to about 8.0, about 6.0 to about 8.0, about 6.5 to about 8.0. In embodiments, the pH of the compositions is between, e.g., about 6.5 to about 7.5, about 7.0 to about 7.8, about 7.2 to about 7.8, or about 7.3 to about 7.6. In embodiments, the pH of the aqueous solution is, e.g., about 6.8, about 7.0, about 7.2, about 7.4, about 7.6, about 7.7, about 7.8, about 8.0, about 8.2, about 8.4, or about 8.6.

In embodiments, parenteral pharmaceutical compositions are provided including gaboxadol, or a pharmaceutically acceptable salt thereof and an excipient wherein the excipient includes a solubilizing agent. For example, solubilizing agents according to the invention may include, e.g., sodium hydroxide, L-lysine, L-arginine, sodium carbonate, potassium carbonate, sodium phosphate, and/or potassium phosphate. The amount of solubilizing agent in the composition will be sufficient such that the solution remains soluble at all concentrations, i.e., does not turn hazy and/or form precipitates.

In embodiments, provided herein are parenteral pharmaceutical compositions including gaboxadol, or a pharmaceutically acceptable salt thereof and an excipient wherein the excipient includes a particulate formation inhibitor. A particulate formation inhibitor refers to a compound that has the desired property of inhibiting the formation of particles in parenteral compositions. Particulate formation inhibitors of the invention include ethylenediaminetetraacetic acid (EDTA) and salts thereof, for example, ethylenediaminetetraacetic acid, calcium disodium salt (preferably as the hydrate); ethylenediaminetetraacetic acid, diammonium salt (preferably as the hydrate); ethylenediaminetetraacetic acid, dipotassium salt (preferably as the dihydrate); ethylenediaminetetraacetic acid, disodium salt (preferably as the dihydrate and, if desired, as the anhydrous form); ethylenediaminetetraacetic acid, tetrasodium salt (preferably as the hydrate); ethylenediaminetetraacetic acid, tripotassium salt (preferably as the dihydrate); ethylenediaminetetraacetic acid, trisodium salt (preferably as the hydrate) and ethylenediaminetetraacetic acid disodium salt, USP(preferably as the dihydrate). In embodiments, parenteral pharmaceutical compositions described herein have an effective amount of a particulate formation inhibitor. In embodiments the excipients may include, e.g., an amino acid, urea, alcohol, ascorbic acid, phospholipids, proteins, such as serum albumin, collagen, and gelatin; salts such as EDTA or EGTA, and sodium chloride, liposomes, polyvinylpyrollidone, sugars, such as dextran, mannitol, sorbitol, and glycerol, propylene glycol and polyethylene glycol (e.g., PEG-4000, PEG-6000), glycerol, glycine, and/or lipids.

In embodiments, provided herein are parenteral pharmaceutical compositions including gaboxadol, or a pharmaceutically acceptable salt thereof and an excipient wherein the excipient includes a solubilizing agent. For example, solubilizing agents may include, but are not limited to, acids, such as carboxylic acids, amino acids. In other examples, the solubilizing agents may be saturated carboxylic acids, unsaturated carboxylic acids, fatty acids, keto acids, aromatic carboxylic acids, dicarboxylic acids, tricarboxylic acids, a-hydroxy acids, amino acids, and combinations thereof.

In embodiments, provided herein are pharmaceutical compositions including gaboxadol or a pharmaceutically acceptable salt thereof and an excipient wherein the excipient includes a solubilizing agent such as formic acid, acetic acid, propionic acid, butyric acid, valeric acid, caproic acid, enanthic acid, caprylic acid, pelargonic acid, capric acid, lauric acid, stearic acid, acrylic acid, docosahexaenoic acid, eicosapentaenoic acid, pyruvic acid, benzoic acid, salicylic acid, aldaric acid, oxalic acid, malonic acid, malic acid, succinic acid, glutaric acid, adipic acid, citric acid, lactic acid, alanine, arginine, asparagine, aspartic acid, cysteine, glutamine, glycine, histidine, isoleucine, leucine, lysine, methionine, phenylalanine, praline, serine, threonine, tryptophan, tyrosine, valine, and combinations thereof. In embodiments, the solubilizing agent is selected from acetic acid, salts thereof, and combinations thereof, (e.g., acetic acid/sodium acetate), citric acid, salts thereof and combinations thereof (e.g., citric acid/sodium citrate), DL arginine, L-arginine and histadine. In embodiments, the solubilizing agent is DL-arginine. In embodiments, the solubilizing agent is L-arginine. In embodiments, the solubilizing agent is acetic acid/sodium acetate. In embodiments, the solubilizing agent is citric acid/sodium citrate.

In embodiments, provided herein are parenteral pharmaceutical compositions including gaboxadol or a pharmaceutically acceptable salt thereof and an excipient wherein the excipient renders the composition isotonic. Isotonic parenteral pharmaceutical compositions herein may be achieved by adding an appropriate quantity of sodium chloride, glucose, laevulose, dextrose, mannitol, or postassium chloride, or calcium chloride, or calcium gluconoglucoheptonate, or mixtures thereof. For example, the excipients may include one or more tonicity agents, such as, e.g., sodium chloride, potassium chloride, glycerin, mannitol, and/or dextrose. Tonicity agents may be used to minimize tissue damage and irritation, reduce hemolysis of blood cells, and/or prevent electrolyte imbalance. For example, the parenteral compositions may be an aqueous solution comprising sodium chloride wherein the composition is isotonic. In embodiments, the isotonizing agent is sodium chloride. In embodiments, the concentration of the isotonizing agent is between about 0.01 and about 2.0 weight percent. In embodiments, the pharmaceutical compositions may comprise up to about 10% isotonizing agent. In embodiments, the parenteral pharmaceutical compositions may comprise up to about, e.g., 0.25%, 0.5%, 1%, 2.5% isotonizing agent. In embodiments the amount of isotonizing agent in the pharmaceutical is between about, e.g., 0.01% to 1%, 0.1% to 1%, 0.25% to 1%, or 0.5% to 1%.

In embodiments, provided herein are parenteral pharmaceutical compositions including gaboxadol, or a pharmaceutically acceptable salt thereof and an excipient wherein the excipient includes a free radical antagonist. In embodiments, the free radical antagonist is ascorbic acid, ascorbic acid derivatives, organic compounds having at least one thiol, alkyl polyhydroxylated, and cycloalkyl polyhydroxylated compounds, and combinations thereof.

In embodiments, provided herein are parenteral pharmaceutical compositions including gaboxadol, or a pharmaceutically acceptable salt thereof and an excipient wherein the excipient includes a preservative. In embodiments, the preservative can be benzalkonium chloride, benzethonium chloride, benzyl alcohol, chlorobutanol, chlorocresol, meta-cresol, phenol, phenylmercuric nitrate, phenylmercuric acetate, methyl p-hydroxybenzoate, propyl p-hydroxybenzoate, butyl p-hydroxybenzoate, or thimerosal. In embodiments, the preservative can be meta-cresol, benzyl alcohol, parabens (e.g., methyl, propyl, butyl), benzalkonium chloride, chlorobutanol, thimerosal, phenylmercuric salts (e.g., acetate, borate, or nitrate), or combinations of any of the above preservatives.

In embodiments, the parenteral pharmaceutical compositions herein include a co-solvent. In some instances, the solubility of gaboxadol may be well below the therapeutic dose and therefore a co-solvent system may be used. A co-solvent is a mixture of solvents that may be used to achieve sufficiently high solubility and may increase the stability. For example, co-solvents may be a water-miscible organic solvent, such as ethanol, propylene, glycol, Capmul PG, propylene glycol, glycerin, polyethylene glycol, sorbitol, dimethylacetamide, and/or dimethylsulfoxide (DMSO). In embodiments, the cosolvent may comprise up to about 75% of the pharmaceutical composition. In other embodiments the amount of cosolvent used include up to about, e.g., 1%, 5%, 10%, 15%, 25%, 40%, 50%, of the parenteral pharmaceutical composition.

In embodiments, stable pharmaceutical compositions suitable for parenteral administration include gaboxadol or a pharmaceutically acceptable salt thereof, in an aqueous solution having an osmolarity between 225 and 350 mOsm/kg and at a pH in the range between 7.0 and 8.0. In embodiments, the aqueous solution has an osmolarity between 270 and 310. In embodiments, the aqueous solution has a pH in the range between 7.2 and 7.8.

The parenteral pharmaceutical compositions may be prepared, for example, by mixing gaboxadol or a pharmaceutically acceptable salt thereof and one or more excipients (e.g., buffering agents, solubilizing agents, tonicity agents, antioxidants, chelating agents, antimicrobial agents and/or preservatives) in a blender under sterile conditions until a uniform blend is obtained. Pre-sterilized vials may then be filled with an appropriate amount of the sterile blend. The predetermined amount of sterile blend may then be mixed with a solvent, e.g., water, saline, about 5-10% sugar (e.g., glucose, dextrose) solution and combinations thereof prior to administration. In addition, the solution may be frozen and thawed prior to further processing.

Parenteral pharmaceutical compositions including gaboxadol or a pharmaceutically acceptable salt thereof, may be prepared by mixing the required amount of gaboxadol or a pharmaceutically acceptable salt thereof which may be purified prior to use in parenteral fluids such as D5W, distilled water, saline or PEG and adjusting the pH of this solution between 6.8-8. The process may be carried out at room temperature, or to increase concentration, the solution may be warmed appropriately. Other solvents such as PEG 400, 600, polypropylene glycol or other glycols can be used to enhance solubility. The resulting solutions after cooling to room temperature, may be sterilized by known means such as ultrafiltration using, e.g., 0.45 micron filter or ethylene oxide treatment or heating and may be packaged into ampules, vials or pre-filled syringes suitable for dispensing a sterile parenteral formulation.

In embodiments, a pharmaceutical composition for parenteral administration is provided wherein the pharmaceutical composition is stable for at least six months. In embodiments, the pharmaceutical compositions herein exhibit no more than about 5% decrease in gaboxadol or pharmaceutically acceptable salt thereof after, e.g., 3 months or 6 months. In embodiments, the amount of gaboxadol or pharmaceutically acceptable salt thereof degradation is no more than about, e.g., 2.5%, 1%, 0.5% or 0.1%. In embodiments, the degradation of gaboxadol or pharmaceutically acceptable salt thereof is less than about, e.g., 5%, 2.5%, 1%, 0.5%, 0.25%, 0.1%, for at least six months.

In embodiments, stable parenteral pharmaceutical compositions are provided in unit dosage form in a vial or ampoule suitable for parenteral administration having a therapeutically effective amount of gaboxadol or pharmaceutically acceptable salt thereof dissolved in sterile water to form a solution wherein the composition is substantially free of any excipient, organic solvent, buffer, acid, base, salt other than gaboxadol or pharmaceutically acceptable salt thereof. In embodiments, the pharmaceutical composition remains sufficiently soluble and is capable of direct administration. In embodiments, the parenteral pharmaceutical composition is capable of storage in the absence of an inert atmosphere for at least six months In embodiments, a parenteral dosage form can include, e.g., from about 1mg to about 500 mg gaboxadol, wherein parenteral administration (e.g., intramuscular, intravenous, subcutaneous, intraperitoneal, or intrathecal) of the dosage form provides an in vivo plasma profile for gaboxadol comprising a mean $AUC_{0-\infty}$ of more than about 25 ng•hr/ml. In embodiments, single dose administration of the dosage form provides an in vivo plasma profile for gaboxadol comprising a mean $AUC_{0-\infty}$ of more than about, e.g., 50 ng•hr/ml, 75 ng•hr/ml, 150 ng•hr/ml, 250 ng•hr/ml, 500 ng•hr/ml, 1000 ng•hr/ml, or 1500 ng•hr/ml. In embodiments, a parenteral pharmaceutical composition includes from about 1 mg to about 500 mg gaboxadol, wherein administration of the parenteral pharmaceutical composition provides an in vivo plasma profile for gaboxadol comprising a mean $C_{max}$ of less than about 10000 ng/ml. In embodiments, single dose administration of a parenteral pharmaceutical composition provides an in vivo plasma profile for gaboxadol of a mean $C_{max}$ of less than about, e.g., 5000 ng/ml, 2500 ng/ml, 1000 ng/ml, 500 ng/ml, 250 ng/ml, or 100 ng/ml.

In embodiments, parenteral compositions containing gaboxadol or a pharmaceutically acceptable salt thereof may be administered as needed, e.g., once, twice, three, four, five, six or more times daily, or continuously depending on the patient's needs. In embodiments, parenteral compositions containing gaboxadol or a pharmaceutically acceptable salt thereof may be administered once and be effective for providing prolonged relief from symptoms of 1p36 deletion syndrome.

When administered, parenteral compositions herein provide a time of maximum plasma concentration ($T_{max}$) for gaboxadol in human patients of about 1 or more hours (e.g., about 1.5 or more hours). In embodiments, a $T_{max}$ of gaboxadol in human patients ranging from between, e.g., about 1 to about 5 hours, about 1 to about 4 hours, about 1 to about 3 hours, about 1 to about 2 hours. In embodiments, a $T_{max}$ for gaboxadol in human patients of more than about 1.5 is observed. In embodiments, a $T_{max}$ for gaboxadol in human patients of less than about 3 hours is observed. The time of maximum plasma concentration is measured once infusion is complete.

In embodiments, pharmaceutical compositions for parenteral administration include gaboxadol or a pharmaceutically acceptable salt thereof wherein parenteral administration exhibits a pharmacokinetic profile of a $T_{max}$ at about 1 to about 120 minutes after administration of the parenteral composition; followed by a plasma drug concentration of at least 50% $C_{max}$ for a duration of about 90 to about 360 minutes. In embodiments, parenteral administration of gaboxadol is followed by a plasma drug concentration of at least 50% $C_{max}$ for a duration of, e.g., about 10 to about 60 minutes, about 15 to about 90 minutes, about 30 to about 120 minutes, about 60 to about 180 minutes, about 90 to about 180 minutes.

Unless defined otherwise, all technical and scientific terms used herein have the same meanings as commonly understood by one of skill in the art to which the disclosure herein belongs.

The term "about" or "approximately" as used herein means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, up to 10%, up to 5%, or up to 1% of a given value. Alternatively, particularly with respect to biological systems or processes, the term can mean within an order of magnitude, preferably within 5-fold, and more preferably within 2-fold, of a value.

"Improvement" refers to the treatment of a subject having 1p36 deletion syndrome measured relative to at least one symptom.

"PK" refers to the pharmacokinetic profile. $C_{max}$ is defined as the highest plasma drug concentration estimated during an experiment (ng/ml) following administration of a drug. $T_{max}$ is defined as the time when $C_{max}$ is estimated (min). $AUC_{0-\infty}$ is the total area under the plasma drug concentration-time curve, from drug administration until the drug is eliminated (ng•hr/ml). The area under the curve is governed by clearance. Clearance is defined as the volume of blood or plasma that is totally cleared of its content of drug per unit time (ml/min).

"Treating" or "treatment" refers to alleviating or delaying the appearance of clinical symptoms of a disease or condition in a subject that may be afflicted with or predisposed to the disease or condition, but does not yet experience or display clinical or subclinical symptoms of the disease or condition. In certain embodiments, "treating" or "treatment" may refer to preventing the appearance of clinical symptoms of a disease or condition in a subject that may be afflicted with or predisposed to the disease or condition, but does not yet experience or display clinical or subclinical symptoms of the disease or condition. "Treating" or "treatment" also refers to inhibiting the disease or condition, e.g., arresting or reducing its development or at least one clinical or subclinical symptom thereof. "Treating" or "treatment" further refers to relieving the disease or condition, e.g., causing regression of the disease or condition or at least one of its clinical or subclinical symptoms. The benefit to a subject to be treated may be statistically significant, mathematically significant, or at least perceptible to the subject and/or the physician. Nonetheless, prophylactic (preventive) and therapeutic (curative) treatment are two separate embodiments of the disclosure herein.

"Pharmaceutically acceptable" refers to molecular entities, formulations and compositions that are "generally regarded as safe", e.g., that are physiologically tolerable and do not typically produce an allergic or similar untoward reaction, such as gastric upset and the like, when administered to a human. In embodiments, this term refers to molecular entities, formulations and compositions approved by a regulatory agency of the federal or a state government, as the GRAS list under section 204(s) and 409 of the Federal Food, Drug and Cosmetic Act, that is subject to premarket review and approval by the FDA or similar lists, the U.S. Pharmacopeia or another generally recognized pharmacopeia for use in animals, and more particularly in humans.

"Effective amount" or "therapeutically effective amount" means a dosage sufficient to alleviate one or more symptom of a disorder, disease, or condition being treated, or to otherwise provide a desired pharmacological and/or physiologic effect.

"Pharmaceutical compositions" and "Pharmaceutical formulations" are used interchangeably herein and include dosage forms and unit doses.

"Patient in need thereof" may include individuals that have been diagnosed with 1p36 deletion syndrome. The methods and/or compositions may be provided to any individual including, e.g., wherein the patient is a neonate, infant (1 month to 6 months), a pediatric patient (6 months to 12 years), an adolescent patient (age 12-18 years) or an adult (over 18 years).

While embodiments of the disclosure have been described and exemplified herein, it is not intended that the disclosure be limited thereto, as it is intended that the disclosure be as broad in scope as the art will allow and that the specification be read likewise. Therefore, the above description should not be construed as limiting, but merely as exemplifications of various embodiments. Those skilled in the art will envision other modifications within the scope and spirit of the claims appended hereto.

What is claimed is:

1. A method for treating 1p36 deletion syndrome comprising administering to a patient in need thereof from about 20 mg to about 50 mg gaboxadol or a pharmaceutically acceptable salt thereof.

2. The method for treating 1p36 deletion syndrome according to claim 1, wherein the gaboxadol or a pharmaceutically acceptable salt thereof is administered once daily.

3. The method for treating 1p36 deletion syndrome according to claim 1, wherein the gaboxadol or a pharmaceutically acceptable salt thereof is administered twice daily.

4. The method for treating 1p36 deletion syndrome according to claim 1, wherein the gaboxadol or a pharmaceutically acceptable salt thereof is administered three times daily.

5. The method for treating 1p36 deletion syndrome according to claim 1, wherein the gaboxadol or a pharmaceutically acceptable salt thereof is administered in a conventional dosage form.

6. The method for treating 1p36 deletion syndrome according to claim 1, wherein the gaboxadol or a pharmaceutically acceptable salt thereof is administered in an orally disintegrating dosage form.

7. A method for treating 1p36 deletion syndrome comprising administering to a patient in need thereof a pharmaceutical composition comprising from about 50 mg to about 250 mg gaboxadol or a pharmaceutically acceptable salt thereof.

8. The method for treating 1p36 deletion syndrome according to claim 7, wherein the pharmaceutical composition is an extended release dosage form.

9. The method for treating 1p36 deletion syndrome according to claim 8, wherein the extended release dosage form releases the gaboxadol or a pharmaceutically acceptable salt thereof for 6 or more hours after administration.

10. The method for treating 1p36 deletion syndrome according to claim 7, wherein the pharmaceutical composition is a delayed release dosage form.

11. The method for treating 1p36 deletion syndrome according to claim 7, wherein the pharmaceutical composition is a pulsatile release dosage form.

12. The method for treating 1p36 deletion syndrome according to claim 8, wherein the extended release dosage form releases the gaboxadol or a pharmaceutically acceptable salt thereof for 12 or more hours after administration.

13. A method for treating 1p36 deletion syndrome comprising administering to a patient aged 1 month to 18 years and in need thereof from about 1 mg to about 50 mg gaboxadol or a pharmaceutically acceptable salt thereof.

14. The method for treating 1p36 deletion syndrome according to claim 13, wherein the gaboxadol or a pharmaceutically acceptable salt thereof is administered once daily.

15. The method for treating 1p36 deletion syndrome according to claim 13, wherein the gaboxadol or a pharmaceutically acceptable salt thereof is administered twice daily.

16. The method for treating 1p36 deletion syndrome according to claim 13, wherein the gaboxadol or a pharmaceutically acceptable salt thereof is administered three times daily.

17. The method for treating 1p36 deletion syndrome according to claim 13, wherein the gaboxadol or a pharmaceutically acceptable salt thereof is administered in a conventional dosage form.

18. The method for treating 1p36 deletion syndrome according to claim 13, wherein the gaboxadol or a pharmaceutically acceptable salt thereof is administered in an orally disintegrating dosage form.

19. The method for treating 1p36 deletion syndrome according to claim 13, wherein the gaboxadol or a pharmaceutically acceptable salt thereof is administered in an extended release dosage form.

20. The method for treating 1p36 deletion syndrome according to claim 13, wherein the gaboxadol or a pharmaceutically acceptable salt thereof is administered in a delayed release dosage form.

21. The method for treating 1p36 deletion syndrome according to claim 13, wherein the gaboxadol or a pharmaceutically acceptable salt thereof is administered in a pulsatile release dosage form.

* * * * *